United States Patent
Beylin et al.

(10) Patent No.: US 7,345,171 B2
(45) Date of Patent: Mar. 18, 2008

(54) ISETHIONATE SALT OF A SELECTIVE CKD4 INHIBITOR

(75) Inventors: Vladimar G. Beylin, Ann Arbor, MI (US); Anthony Clyde Blackburn, Saline, MI (US); David Thomas Erdman, Holland, MI (US); Peter Laurence Toogood, Ann Arbor, MI (US)

(73) Assignee: Warner-Lambert Company LLC, Morris Plains, NJ (US)

( * ) Notice: Subject to any disclaimer, the term of this patent is extended or adjusted under 35 U.S.C. 154(b) by 511 days.

(21) Appl. No.: 10/884,927

(22) Filed: Jul. 6, 2004

(65) Prior Publication Data

US 2005/0059670 A1  Mar. 17, 2005

Related U.S. Application Data

(60) Provisional application No. 60/486,351, filed on Jul. 11, 2003.

(51) Int. Cl.
*C07D 471/04* (2006.01)
*C07D 487/04* (2006.01)
(52) U.S. Cl. .................................................... 544/279
(58) Field of Classification Search .................. 544/279
See application file for complete search history.

(56) References Cited

U.S. PATENT DOCUMENTS 6,936,612 B2 * 8/2005 Barvian et al. ......... 514/252.16
7,208,489 B2 * 4/2007 Barvian et al. ......... 514/217.06

FOREIGN PATENT DOCUMENTS

WO   WO 03/062236   7/2003

OTHER PUBLICATIONS

BBC News/Health, Killer Breast Cancer Therapy Hope, Jan. 21, 2006.*

(Continued)

*Primary Examiner*—Mark L Berch
*Assistant Examiner*—Cecilia M Jaisle
(74) *Attorney, Agent, or Firm*—Bryan C. Zielinski; Wendy L. Hsu

(57) ABSTRACT

Disclosed are polymorphs of the isethionate salt of 6-acetyl-8-cyclopentyl-5-methyl-2-(5-piperazin-1-yl-pyridin-2-ylamino)-8H-pyrido[2,3-d]pyrimidin-7-one,

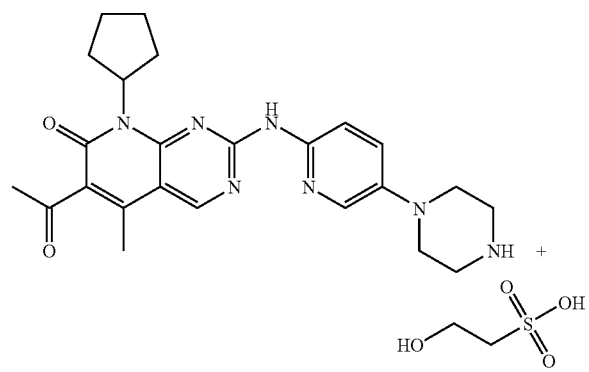

which is a selective cyclin-dependent kinase 4 (CDK4) inhibitor useful for treating inflammation and cell proliferative diseases such as cancer and restenosis.

10 Claims, 10 Drawing Sheets

OTHER PUBLICATIONS

Rane, et al., Nature America, vol. 22, pp. 44-52, May 1999.*

Blain, et al., J. Biol. Chem., vol. 272, No. 41, 1997, pp. 25863-25872.*

Fischer, P., et al., "Recent Advances And New Directions In The Discovery And Development Of Cyclin-Dependent Kinase Inhbitors ," *Current Opinion in Drug Discovery*, 2001, 623-634, vol. 4.

Fry, D., et al., "Inhibitors Of cyclin-Dependent Kinases As Therapeutic Agents For The Treatment Of Cancer," *Current Opinion In Oncologic, Endocrine & Matabolic Invest*igational Drugs, 2000, 40-59, vol. 2, No. 1.

Sielecki, T., et al., "Cyclin-Dependent Kinase Inhibitors: Useful Targets In Cell Cycle Regulation," *Journal of Medicinal Chemistry*, 2000, 1-18, vol. 43, No. 1.

Webster, K., et al., "Novel Drugs Targeting The Cell Cycle," *Emerging Drugs*, 2000, 45-59, vol. 5, No. 1.

Ministerial Order for Lebanese Patent No. 6633, Official Gazette No. 28, Jun. 19, 2003, 4382-4383.

* cited by examiner

ISETHIONATE SALT OF A SELECTIVE CKD4 INHIBITOR

The present application claims the benefit of U.S. Provisional Patent Application No. 60/486,351, filed Jul. 11, 2003, the contents of which are hereby incorporated by reference.

BACKGROUND OF THE INVENTION

1. Field of Invention

This invention relates to salt forms of 6-acetyl-8-cyclopentyl-5-methyl-2-(5-piperazin-1-yl-pyridin-2-ylamino)-8H-pyrido[2,3-d]pyrimidin-7-one, which is a selective cyclin-dependent kinase 4 (CDK4) inhibitor that is useful for treating inflammation and cell proliferative diseases such as cancer and restenosis.

2. Discussion

Cyclin-dependent kinases and related serine/threonine protein kinases are important cellular enzymes that perform essential functions in regulating cell division and proliferation. The cyclin-dependent kinase catalytic units are activated by regulatory subunits known as cyclins. At least sixteen mammalian cyclins have been identified (D. G. Johnson and C. L. Walker, *Annu. Rev. Pharmacol. Toxicol.* (1999) 39:295-312). Cyclin B/CDK1, Cyclin A/CDK2, Cyclin E/CDK2, Cyclin D/CDK4, Cyclin D/CDK6, and probably other heterodimers including CDK3 and CDK7 are important regulators of cell cycle progression. Additional functions of Cyclin/CDK heterodimers include regulation of transcription, DNA repair, differentiation and apoptosis (D. O. Morgan, *Annu. Rev. Cell. Dev. Biol.* (1997) 13261-13291).

Cyclin-dependent kinase inhibitors may prove useful in treating cancer. Increased activity or temporally abnormal activation of cyclin-dependent kinases has been shown to result in the development of human tumors (C. J. Sherr, *Science* (1996) 274:1672-1677). Indeed, human tumor development is commonly associated with alterations in either the CDK proteins themselves or their regulators (C. Cordon-Cardo, *Am. J. Pathol.* (1995) 147:545-560; J. E. Karp and S. Broder, *Nat. Med.* (1995) 1:309-320; M. Hall et al., *Adv. Cancer Res.* (1996) 68:67-108). Naturally occurring protein inhibitors of CDKs such as p16 and p27 cause in vitro growth inhibition in lung cancer cell lines (A. Kamb, *Curr. Top. Microbiol. Immunol.* (1998) 227:139-148).

Small molecule CDK inhibitors may also be used in the treatment of cardiovascular disorders such as restenosis and atherosclerosis and other vascular disorders that are due to aberrant cell proliferation. Vascular smooth muscle proliferation and intimal hyperplasia following balloon angioplasty are inhibited by over-expression of the cyclin-dependent kinase inhibitor protein p21 (M. W. Chang et al., *J. Clin. Invest.* (1995) 96:2260; Z-Y. Yang et al., *Proc. Natl. Acad. Sci.* (*USA*) (1996) 93:9905). Moreover, the purine CDK2 inhibitor CVT-313 (Ki=95 nM) resulted in greater than 80% inhibition of neointima formation in rats (E. E. Brooks et al., *J. Biol. Chem.* (1997) 29207-29211).

CDK inhibitors can be used to treat diseases caused by a variety of infectious agents, including fungi, protozoan parasites such as *Plasmodium falciparum*, and DNA and RNA viruses. For example, cyclin-dependent kinases are required for viral replication following infection by herpes simplex virus (HSV) (L. M. Schang et al., *J. Virol.* (1998) 72:5626) and CDK homologs are known to play essential roles in yeast.

Selective CDK inhibitors can be used to ameliorate the effects of various autoimmune disorders. Rheumatoid arthritis, a chronic inflammatory disease, is characterized by synovial tissue hyperplasia. Inhibition of synovial tissue proliferation should minimize inflammation and prevent joint destruction. Expression of the CDK inhibitor protein p16 in synovial fibroblasts has been found to inhibit growth (K. Taniguchi et al., *Nat. Med.* (1999) 5:760-767). Similarly, in a rat model of arthritis, joint swelling was substantially inhibited by treatment with a p16 expressing adenovirus. CDK inhibitors may be effective against other disorders of cell proliferation including psoriasis (characterized by keratinocyte hyperproliferation), glomerulonephritis, and lupus.

Certain CDK inhibitors may be useful as chemoprotective agents through their ability to inhibit cell cycle progression of normal untransformed cells (Chen et al. *J. Natl. Cancer Institute* (2000) 92:1999-2008). Pre-treatment of a cancer patient with a CDK inhibitor prior to the use of cytotoxic agents can reduce the side effects commonly associated with chemotherapy. Normal proliferating tissues are protected from the cytotoxic effects by the action of the selective CDK inhibitor.

Review articles on small molecule inhibitors of cyclin-dependent kinases have noted the difficulty of identifying compounds that inhibit specific CDK proteins without inhibiting other enzymes. Thus, despite their potential to treat a variety of diseases, no CDK inhibitors are currently approved for commercial use (P. M. Fischer, *Curr. Opin. Drug Discovery* (2001) 4:623-634; D. W. Fry and M. D. Garrett, *Curr. Opin. Oncologic, Endocrine & Metabolic Invest.* (2000) 2:40-59; K. R. Webster and D. Kimball, *Emerging Drugs* (2000) 5:45-59; T. M. Sielecki et al., *J. Med. Chem.* (2000) 43:1-18.).

Despite these difficulties, recent studies have identified a number of selective CDK4 inhibitors that, as discussed above, may prove useful in treating cancer—either as anticancer agents or as chemoprotective agents—and in treating cardiovascular disorders, such as restenosis and atherosclerosis, diseases caused by infectious agents, and autoimmune disorders, including rheumatoid arthritis. For a disclosure of these selective CDK4 inhibitors, see commonly assigned International Patent Application PCT/IB03/00059, filed Jan. 10, 2003 (the '059 application), which is herein incorporated by reference in its entirety for all purposes.

The '059 application discloses a particularly potent and selective CDK4 inhibitor, 6-acetyl-8-cyclopentyl-5-methyl-2-(5-piperazin-1-yl-pyridin-2-ylamino)-8H-pyrido[2,3-d]pyrimidin-7-one:

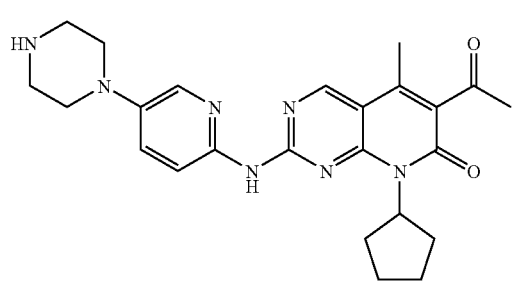

1

In standard enzyme assays the compound of Formula 1 exhibits $IC_{50}$ concentrations for CDK4 and CDK2 inhibition (at 25° C.) of 0.011 μM and >5 μM, respectively. For a discussion of standard CDK4 and CDK2 assays for $IC_{50}$ determinations, see D. W. Fry et al., *J. Biol. Chem.* (2001) 16617-16623.

Though the compound of Formula 1 is a potent and selective CDK4 inhibitor, its use in pharmaceutical products presents challenges. For example, the free base has poor water solubility (9 μg/mL) and exhibits low bioavailability in animal studies. A di-HCl salt of the compound of Formula 1 appears to exhibit adequate water solubility. However, moisture uptake studies reveal that, even at low relative humidity (10% RH), the di-HCl salt absorbs water in an amount greater than about 2% of its mass, making it unsuitable for use in a solid drug product. A mono-HCl salt of the compound of Formula 1 is marginally hygroscopic, absorbing more than 2% of its mass at a relative humidity above 80%. However, the process for preparing the mono-HCl salt yields partially crystalline drug substance, indicating potential problems with process scale-up. Other salt forms of the compound of Formula 1 are thus needed.

SUMMARY OF THE INVENTION

The present invention provides a mono-isethionate salt of 6-acetyl-8-cyclopentyl-5-methyl-2-(5-piperazin-1-yl-pyridin-2-ylamino)-8H-pyrido[2,3-d]pyrimidin-7-one, which is represented by Formula 2:

2

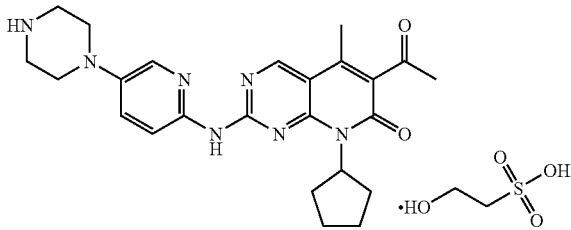

The isethionate salt can exist as one or more polymorphs, including Form A, Form B, and Form D. Each of the polymorphs can be distinguished by its powder X-ray diffraction (PXRD) pattern (diffractogram), or Raman spectrum, or differential scanning calorimetry (DSC) thermogram, or some combination of PXRD pattern, Raman spectrum, and DSC thermogram. The isethionate salt may be anhydrous, or may contain varying amounts of water or one or more solvents.

Thus, one aspect of the present invention provides a mono-isethionate salt of 6-acetyl-8-cyclopentyl-5-methyl-2-(5-piperazin-1-yl-pyridin-2-ylamino)-8H-pyrido[2,3-d]pyrimidin-7-one, which is designated as Form A, and is characterized by one or more of the following: a powder X-ray diffraction pattern having peaks at 2θ values of about 8.7, 13.5, and 17.6, or a Raman spectrum having peaks at Raman Shift values of about 1600 $cm^{-1}$, 1290 $cm^{-1}$, 675 $cm^{-1}$, 470 $cm^{-1}$, 450 $cm^{-1}$, and 425 $cm^{-1}$, or a DSC thermogram having a sharp endotherm at 273° C.

Another aspect of the present invention provides a mono-isethionate salt of 6-acetyl-8-cyclopentyl-5-methyl-2-(5-piperazin-1-yl-pyridin-2-ylamino)-8H-pyrido[2,3-d]pyrimidin-7-one, which is designated as Form B, and is characterized by one or more of the following: a powder X-ray diffraction pattern having peaks at 2θ values of about 5.1, 11.8, 12.1, 12.8, 13.1, and 14.7, a Raman spectrum having peaks at Raman Shift values of about 1600 $cm^{-1}$, 1290 $cm^{-1}$, 470 $cm^{-1}$, 450 $cm^{-1}$, and 425 $cm^{-1}$, but no substantial peak at 675 $cm^{-1}$, or a DSC thermogram having a sharp endotherm at 271° C.

A further aspect of the present invention provides a mono-isethionate salt of 6-acetyl-8-cyclopentyl-5-methyl-2-(5-piperazin-1-yl-pyridin-2-ylamino)-8H-pyrido[2,3-d]pyrimidin-7-one, which is designated as Form D, and is characterized by one or more of the following: a powder X-ray diffraction pattern having peaks at 2θ values of about 8.4, 8.9, and 21.9, a Raman spectrum having a peak at a Raman Shift value of about 463 $cm^{-1}$, or a DSC thermogram having a sharp endotherm at 277° C. For each salt form, the powder X-ray diffraction pattern is obtained using $CuK_\alpha$ radiation and the DSC thermogram is obtained using a heating rate of 5° C./min.

The present invention also provides pharmaceutical dosage forms that include an isethionate salt of 6-acetyl-8-cyclopentyl-5-methyl-2-(5-piperazin-1-yl-pyridin-2-ylamino)-8H-pyrido[2,3-d]pyrimidin-7-one and one or more pharmaceutically acceptable excipients. Useful excipients include disintegrants, binders, diluents, surface-active agents, lubricants, preservatives, anti-oxidants, flavors, colorants, and the like.

The present invention also provides methods of making the isethionate salt of 6-acetyl-8-cyclopentyl-5-methyl-2-(5-piperazin-1-yl-pyridin-2-ylamino)-8H-pyrido[2,3-d]pyrimidin-7-one. One method includes adding a solution of isethionic acid and a first solvent to an aqueous slurry of 6-acetyl-8-cyclopentyl-5-methyl-2-(5-piperazin-1-yl-pyridin-2-ylamino)-8H-pyrido[2,3-d]pyrimidin-7-one, to produce a first mixture. The method also includes freeze-drying the mixture to give an amorphous salt, which is subsequently combined with a second solvent to produce a second mixture that includes the isethionate salt of 6-acetyl-8-cyclopentyl-5-methyl-2-(5-piperazin-1-yl-pyridin-2-ylamino)-8H-pyrido[2,3-d]pyrimidin-7-one.

Another method includes providing a seed crystal of an isethionate salt form of 6-acetyl-8-cyclopentyl-5-methyl-2-(5-piperazin-1-yl-pyridin-2-ylamino)-8H-pyrido[2,3-d]pyrimidin-7-one, and adding the seed crystal to a dispersion of 6-acetyl-8-cyclopentyl-5-methyl-2-(5-piperazin-1-yl-pyridin-2-ylamino)-8H-pyrido[2,3-d]pyrimidin-7-one and a first solvent to produce a first mixture. The method also includes combining the first mixture with a solution of isethionic acid and a second solvent to produce a second mixture, which includes the isethionate salt of 6-acetyl-8-cyclopentyl-5-methyl-2-(5-piperazin-1-yl-pyridin-2-ylamino)-8H-pyrido[2,3-d]pyrimidin-7-one.

In both of the above methods, the first and second solvents may be the same or different, and are water-miscible solvents, including MeOH, EtOH, and other alcohols. To improve yields, the methods may include heating, cooling, or heating and cooling the second mixture to temperatures above and below room temperature. For instance, the second mixture may be heated to a temperature ranging from about 30° C. to about 60° C. and subsequently allowed to cool to room temperature. Alternatively, the second mixture may be allowed to stand at room temperature, and subsequently cooled to a temperature at or below about 0° C. Similarly, the second mixture may be heated to a temperature ranging from about 30° C. to about 60° C. and subsequently cooled to a temperature at or below about 0° C.

Another method includes reacting 4-{6-[6-(1-butoxy-vinyl)-8-cyclopentyl-5-methyl-7-oxo-7,8-dihydro-pyrido[2,3-d]pyrimidin-2-ylamino]-pyridin-3-yl}-piperazine-1-carboxylic acid tert-butyl ester with isethionic acid in a solvent and water to give a mixture that includes a di-isethionate salt of 6-acetyl-8-cyclopentyl-5-methyl-2-(5-piperazin-1-yl-pyridin-2-ylamino)-8H-pyrido[2,3-d]pyrimidin-7-one. The method optionally includes adding a hindered base to the reaction mixture to generate a mono-isethionate salt of 6-acetyl-8-cyclopentyl-5-methyl-2-(5-piperazin-1-yl-pyridin-2-ylamino)-8H-pyrido[2,3-d]pyrimidin-7-one.

The present invention further provides a method of treating a disorder or condition in a mammal, including a human, caused by abnormal cell proliferation, or by viral or fungal infections, or by an autoimmune disease. The method includes administering to the mammal an amount of an isethionate salt of 6-acetyl-8-cyclopentyl-5-methyl-2-(5-piperazin-1-yl-pyridin-2-ylamino)-8H-pyrido[2,3-d]pyrimidin-7-one, which is effective in treating the disorder or condition. Disorders or conditions caused by abnormal cell proliferation include cancer and vascular smooth muscle proliferation associated with atherosclerosis, post-surgical vascular stenosis and restenosis, and endometriosis. Autoimmune diseases include psoriasis, inflammation-like rheumatoid arthritis, lupus, type 1 diabetes, diabetic nephropathy, multiple sclerosis, glomerulonephritis, and organ transplant rejection, including host versus graft disease.

The isethionate salt provides significant advantages over the free base (Formula 1) and other salt forms, including mono- and di-HCl addition salts. Compared to the free base, the isethionate salt exhibits over a 20,000-fold improvement in water solubility. Unlike the case of the di-HCl salt, however, the improvement in solubility is not accompanied by a substantial increase in hygroscopicity. Additionally, the isethionate salt is substantially crystalline, and therefore does not suffer from potential scale-up issues associated with the mono-HCl salt. These and other advantages should help alleviate many of the challenges facing development of pharmaceutical products containing the selective CDK4 inhibitor of Formula 1.

BRIEF DESCRIPTION OF THE DRAWINGS

The various features, advantages and other uses of the present invention will become more apparent by referring to the following description and drawings in which.

DETAILED DESCRIPTION DEFINITIONS AND ABBREVIATIONS

Figure 1:
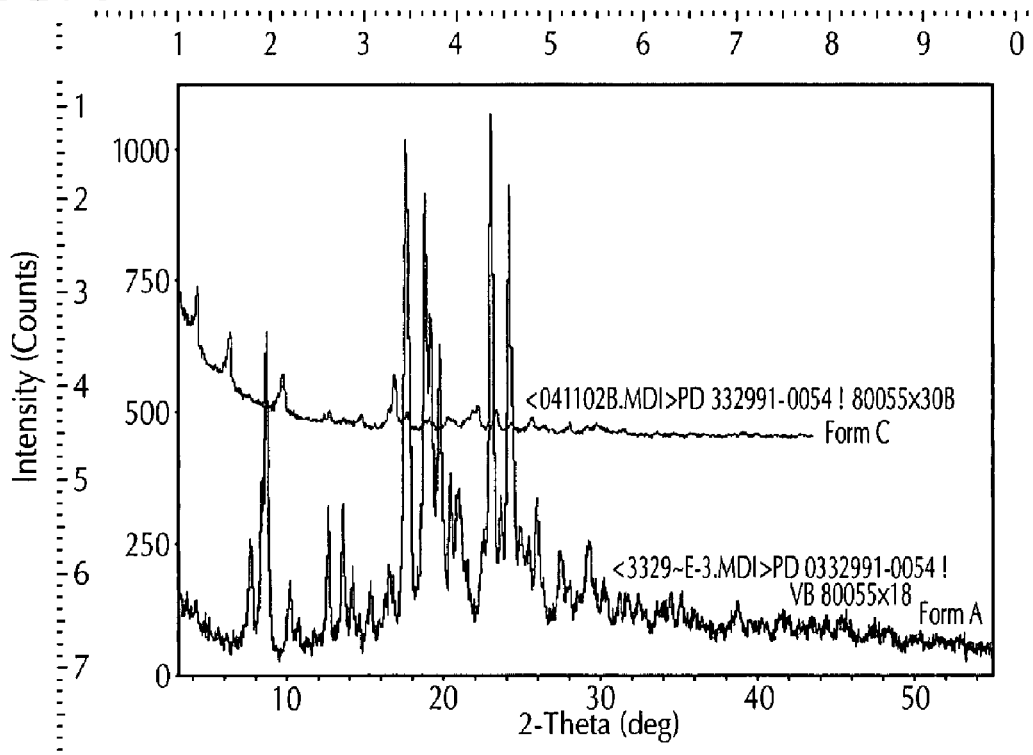
FIG. 1 shows a PXRD pattern of a mono-isethionate salt (Form A) of 6-acetyl-8-cyclopentyl-5-methyl-2-(5-piperazin-1-yl-pyridin-2-ylamino)-8H-pyrido[2,3-d]pyrimidin-7-one.

Unless otherwise indicated, this disclosure uses definitions provided below.

The term "cancer" includes, but is not limited to, the following cancers: cancers of the breast, ovary, cervix, prostate, testis, esophagus, stomach, skin, lung, bone, colon, pancreas, thyroid, biliary passages, buccal cavity and pharynx (oral), lip, tongue, mouth, pharynx, small intestine, colon-rectum, large intestine, rectum, brain and central nervous system, glioblastoma, neuroblastoma, keratoacanthoma, epidermoid carcinoma, large cell carcinoma, adenocarcinoma, adenocarcinoma, adenoma, adenocarcinoma, follicular carcinoma, undifferentiated carcinoma, papillary carcinoma, seminoma, melanoma, sarcoma, bladder carcinoma, liver carcinoma, kidney carcinoma, myeloid disorders, lymphoid disorders, Hodgkin's disease, hairy cells, and leukemia.

The phrase "pharmaceutically acceptable" refers to substances, which are within the scope of sound medical judgment, suitable for use in contact with the tissues of patients without undue toxicity, irritation, allergic response, and the like, commensurate with a reasonable benefit/risk ratio, and effective for their intended use.

The term "treating" refers to reversing, alleviating, inhibiting the progress of, or preventing a disorder or condition to which such term applies, or to preventing one or more symptoms of such disorder or condition.

The term "treatment" refers to the act of "treating," as defined immediately above.

Table 1 lists abbreviations used through the specification.

TABLE 1

Abbreviations

| Abbreviation | Description |
| --- | --- |
| aq | aqueous |
| ACN | acetonitrile |
| BOC | tert-butoxycarbonyl |
| DCM | dichloromethane |
| DSC | differential scanning calorimetry |
| Et₃N | triethylamine |
| EtOH | ethyl alcohol |
| h, min, s | hour, minute, second |
| IPA | isopropyl alcohol |
| MeOH | methanol |
| PXRD | powder X-ray diffraction |
| RH | relative humidity |
| RT | room temperature, i.e. 20° C.-25° C. |
| THF | tetrahydrofuran |
| mgA/mL | milligrams of active substance per milliliter of solution |

The mono-isethionate salt (Formula 2) can exist as one or more polymorphs, including Form A, Form B, and Form D. As indicated above, each of the polymorphs may be distinguished by powder X-ray diffraction (PXRD), or Raman spectroscopy, or differential scanning calorimetry (DSC), or some combination of these characterization methods. The mono-isethionate salt (Formula 2) may be anhydrous, or may contain varying amounts of water or one or more solvents. Furthermore, the mono-isethionate salt (Formula 2) may be substantially pure—i.e., contain at least about 99 wt % of a particular polymorph—or may be a mixture of two or more of the polymorphs (e.g., Form B and Form D, etc.).

The free base (Formula 1) is a dibasic compound, which may form both mono- and di-acid addition salts. Its conjugate acid has $pK_a$s of 7.3 and 4.1, so comparatively strong acids are necessary for generating the di-salt. Though it may be possible to form a di-isethionate salt of the compound of Formula 1, the mono-isethionate salt appears to be more useful since it requires less counter ion.

Figure 2:
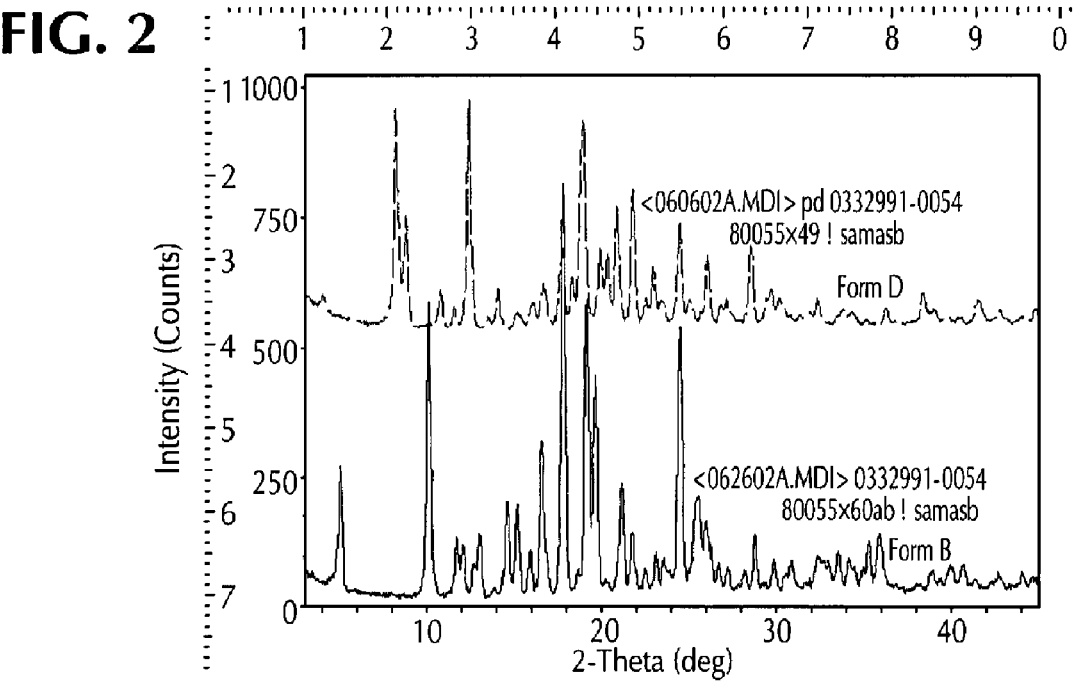
FIG. 2 shows PXRD patterns of a mono-isethionate salt (Form B and Form D) of 6-acetyl-8-cyclopentyl-5-methyl-2-(5-piperazin-1-yl-pyridin-2-ylamino)-8H-pyrido[2,3-d]pyrimidin-7-one.
Figure 3:
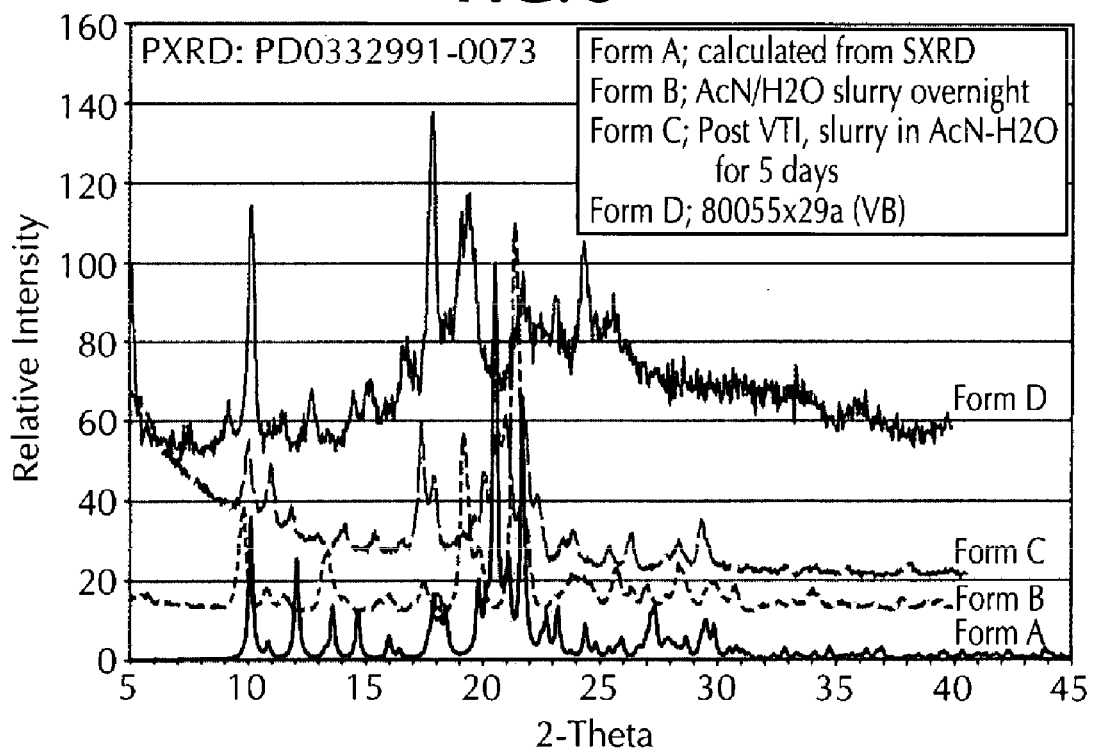
FIG. 3 shows a PXRD pattern of a mono-mesylate salt (Form A, Form B, Form C, and Form D) of 6-acetyl-8-cyclopentyl-5-methyl-2-(5-piperazin-1-yl-pyridin-2-ylamino)-8H-pyrido[2,3-d]pyrimidin-7-one.
Figure 4:
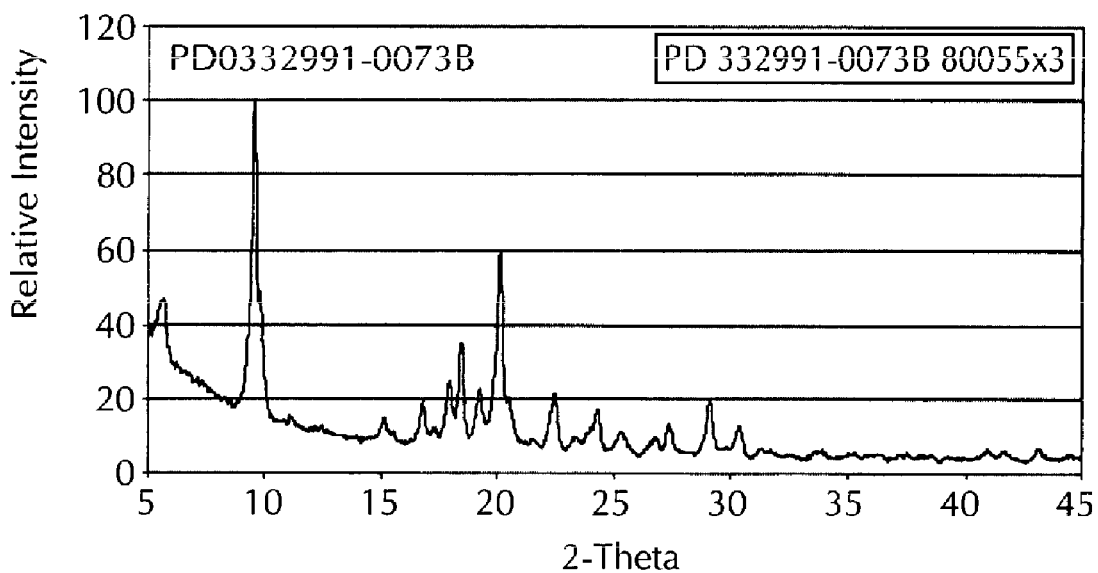
FIG. 4 shows a PXRD pattern of a di-mesylate salt of 6-acetyl-8-cyclopentyl-5-methyl-2-(5-piperazin-1-yl-pyridin-2-ylamino)-8H-pyrido[2,3-d]pyrimidin-7-one.
Figure 5:
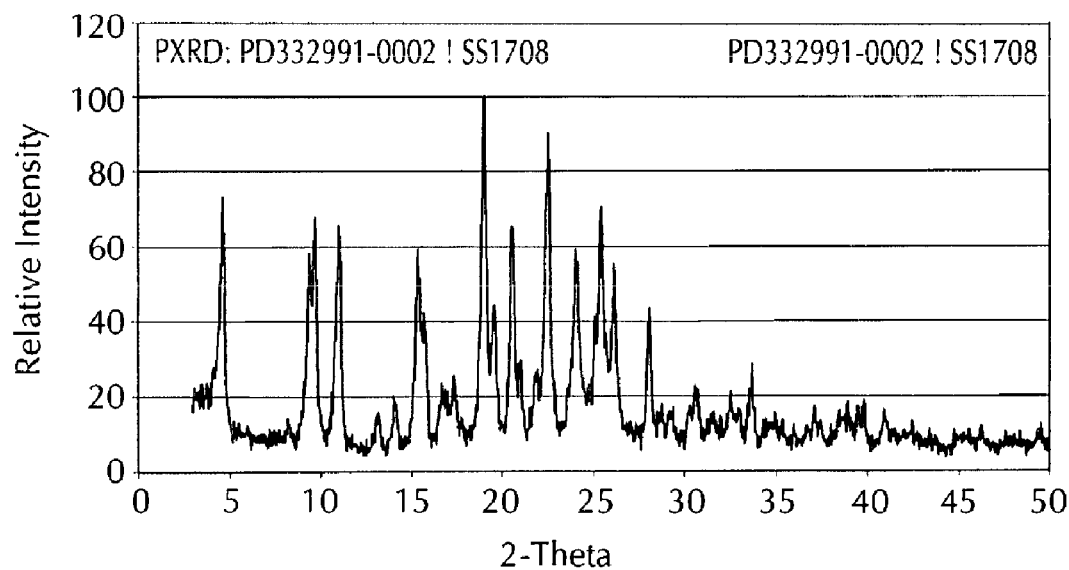
FIG. 5 shows a PXRD pattern of a mono-HCl salt of 6-acetyl-8-cyclopentyl-5-methyl-2-(5-piperazin-1-yl-pyridin-2-ylamino)-8H-pyrido[2,3-d]pyrimidin-7-one.
Figure 6:
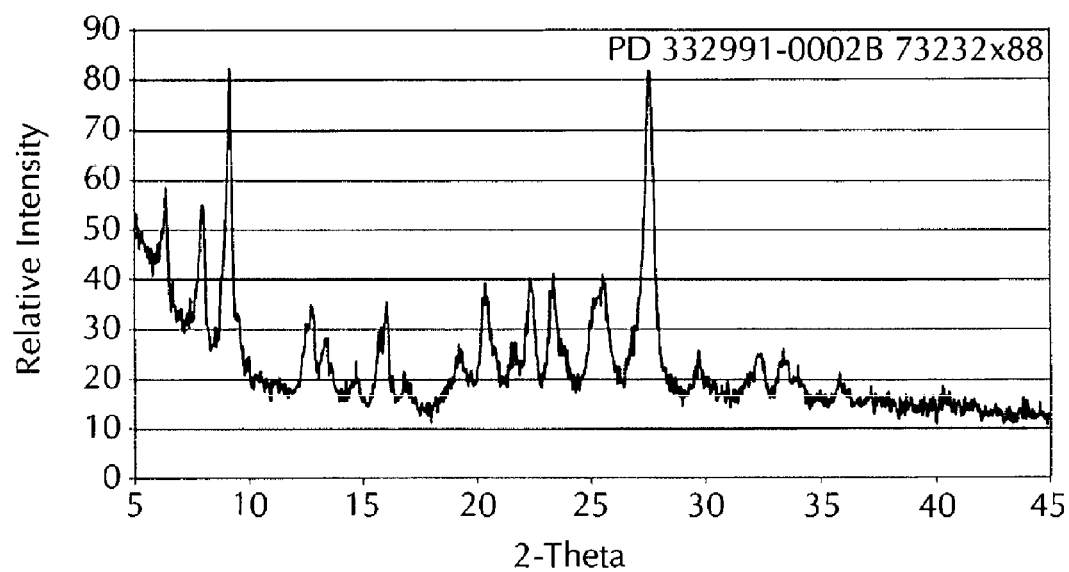
FIG. 6 shows a PXRD pattern of a di-HCl salt of 6-acetyl-8-cyclopentyl-5-methyl-2-(5-piperazin-1-yl-pyridin-2-ylamino)-8H-pyrido[2,3-d]pyrimidin-7-one.

FIG. 1 and FIG. 2 provide PXRD diffractograms for mono-isethionate salt forms of 6-acetyl-8-cyclopentyl-5-methyl-2-(5-piperazin-1-yl-pyridin-2-ylamino)-8H-pyrido[2,3-d]pyrimidin-7-one (Formula 2). These forms are designated as Form A in FIG. 1 and Form B and Form D in FIG. 2. To improve readability, the diffractogram of Form D in FIG. 2 has been shifted upward about 700 units. Table 2, below, lists significant PXRD peaks (i.e., those exhibiting peak height to noise ratio greater than 3.5.) for mono-isethionate polymorphs A, B, and D, and provides in underlined font, a subset of characteristic peaks that may be used to distinguish one polymorph from another. The list of characteristic peaks provided in Table 2 is not the only possible list of characteristic peaks. Persons of ordinary skill in the art of polymorph identification may choose other sets of characteristic peaks that will also distinguish one polymorph from another.

For comparison purposes, FIG. 3-FIG. 6 show PXRD diffractograms for, respectively, mono-mesylate, di-mesylate, mono-HCl, and di-HCl salts of 6-acetyl-8-cyclopentyl-5-methyl-2-(5-piperazin-1-yl-pyridin-2-ylamino)-8H-pyrido[2,3-d]pyrimidin-7-one. Although these salts may exist in more than one form, distinct polymorphs have only been identified for the mono-mesylate salt, which FIG. 3 designates as Form A, Form B, Form C, and Form D. To highlight differences among the mono-mesylate salt forms, the diffractograms of Form B, Form C, and Form D in FIG. 3 have been shifted upward by various amounts.

Each of the PXRD patterns shown in FIG. 1-FIG. 6 were obtained on a RIGAKU D/Max 2200 powder X-ray diffractometer using $CuK_\alpha$ radiation. The diffractometer was equipped with a fine-focus X-ray tube. During each run, the tube voltage and current were set at 40 kV and 40 mA, respectively, the divergence and scattering slits were set at 0.50°, and the receiving slit was set at 0.3 mm. Diffracted radiation was detected using a NaI scintillation detector. For each of the runs, a θ-2θ continuous scan of approximately 1°/min (3 s/0.040° step) from 3.0 to 40.0° 2θ was used. Samples were prepared for analysis by placing them in a silicon-wafer holder. Data were collected using RIGAKU's RIGMEAS software and were analyzed using a proprietary software package developed using the JADE software platform.

For each powder X-ray diffraction measurement, a sample of a salt form was placed into a cavity located on a planar surface of the holder, and a glass slide was used to level the surface of the sample. The holder, which contains the sample, was placed in the diffractometer, and the source of the X-ray beam irradiated the sample, initially at a small angle relative to the planar surface of the holder. The X-ray beam was subsequently moved through an arc in a step-wise manner, which successively increased the angle between the incident beam and the planar surface of the holder. At each step of the scan, the scintillation counter detected the amount of diffracted radiation, which was recorded as a function of 2θ. The instrument software displays the diffracted radiation results of the scan as intensity versus 2θ (FIG. 1-FIG. 6).

Differences in PXRD patterns among separate measurements of the same polymorph may arise for many reasons. Sources of error include variations in sample preparation (e.g. sample height), instrument errors, calibration errors, and operator errors (including errors in determining peak locations). Preferential orientation, i.e., a lack of random orientation of crystals in the PXRD sample, can result in significant differences in relative peak heights. Calibration errors and sample height errors often result in a shift of all of the peaks of the diffractogram in the same direction and by the same amount. Small differences in sample height on a flat holder may lead to large displacements in PXRD peak positions. For a systematic study showing that sample height differences of 1 mm may lead to peak shifts as high as 1° 2θ, see Chen et al., *J. Pharmaceutical and Biomedical Analysis* (2001) 26:63.

In many instances, peak shifts among diffraction patterns resulting from systematic error can be eliminated by compensating for the shift (e.g., applying a correction factor to all peak position values) or by recalibrating the diffractometer. Generally, the same techniques can be used to compensate for differences among diffractometers so that PXRD peak positions obtained from two different instruments can be brought into agreement. Furthermore, when these techniques are applied to PXRD measurements from the same or different diffractometers, the peak positions for a particular polymorph will usually agree to within about ±0.2° 2θ.

TABLE 2

Significant PXRD Peaks for Mono-Isethionate Salt Form A, B, and D

| Polymorph | Significant Peaks, 2θ (Underlined values are characteristic of a particular polymorph) |
|---|---|
| A | 8.7, 12.6, 13.5, 17.6, 18.8, 19.6, 19.8, 23.0, 24.2 |
| B | 5.1, 10.2, 11.8, 12.1, 12.8, 13.1, 14.7, 15.2, 16.0, 16.6, 17.9, 19.2, 19.7, 21.3, 21.9, 22.6, 23.2, 24.6, 25.6, 26.1, 28.9, 30.0, 30.9, 32.5, 33.0, 32.5, 33.0, 34.2, 35.3, 36.0 |
| D | 8.4, 8.9, 10.8, 12.6, 14.2, 16.8, 17.9, 18.4, 19.1, 20.0, 20.4, 21.0, 21.9, 22.6, 23.0, 23.6, 24.6, 26.2, 27.2, 28.7, 29.8, 30.3, 38.4 |

Figure 7:
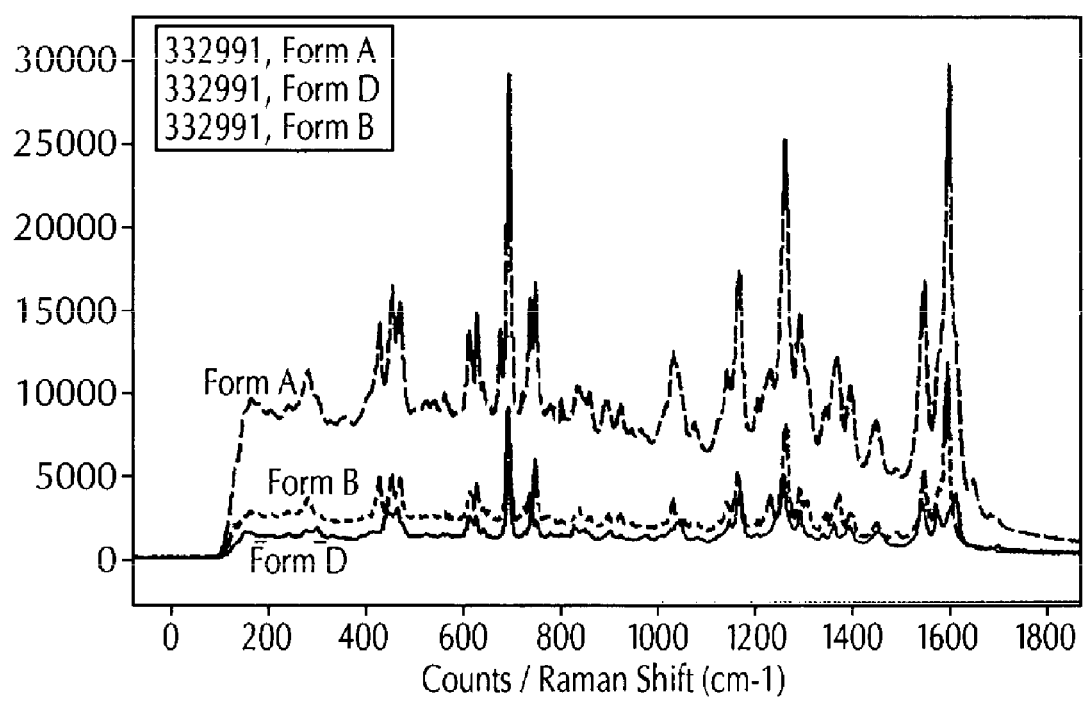
FIG. 7 shows Raman spectra of a mono-isethionate salt (Form A, Form B, and Form D) of 6-acetyl-8-cyclopentyl-5-methyl-2-(5-piperazin-1-yl-pyridin-2-ylamino)-8H-pyrido[2,3-d]pyrimidin-7-one, having Raman Shifts ranging from 0 cm$^{-1}$ to 1850 cm$^{-1}$.
Figure 8:
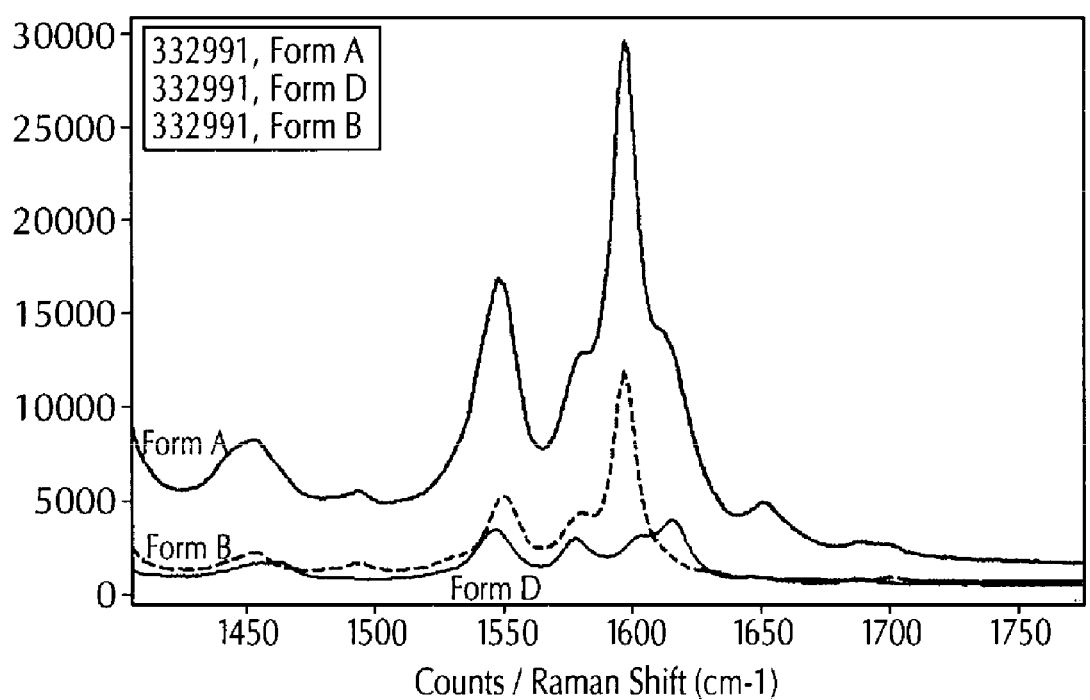
FIG. 8 shows Raman spectra of a mono-isethionate salt (Form A, Form B, and Form D) of 6-acetyl-8-cyclopentyl-5-methyl-2-(5-piperazin-1-yl-pyridin-2-ylamino)-8H-pyrido[2,3-d]pyrimidin-7-one, having Raman Shifts ranging from 1350 cm$^{-1}$ to 1800 cm$^{-1}$.
Figure 9:
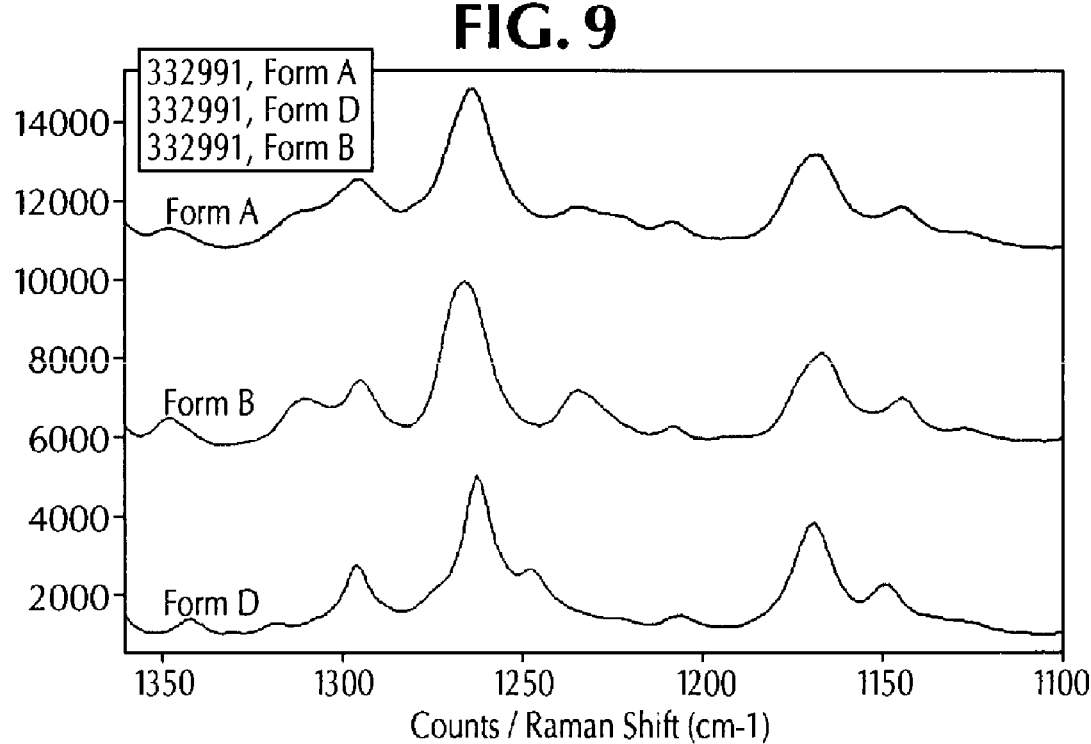
FIG. 9 shows Raman spectra of a mono-isethionate salt (Form A, Form B, and Form D) of 6-acetyl-8-cyclopentyl-5-methyl-2-(5-piperazin-1-yl-pyridin-2-ylamino)-8H-pyrido[2,3-d]pyrimidin-7-one, having Raman Shifts ranging from 1100 cm$^{-1}$ to 1350 cm$^{-1}$.
Figure 10:
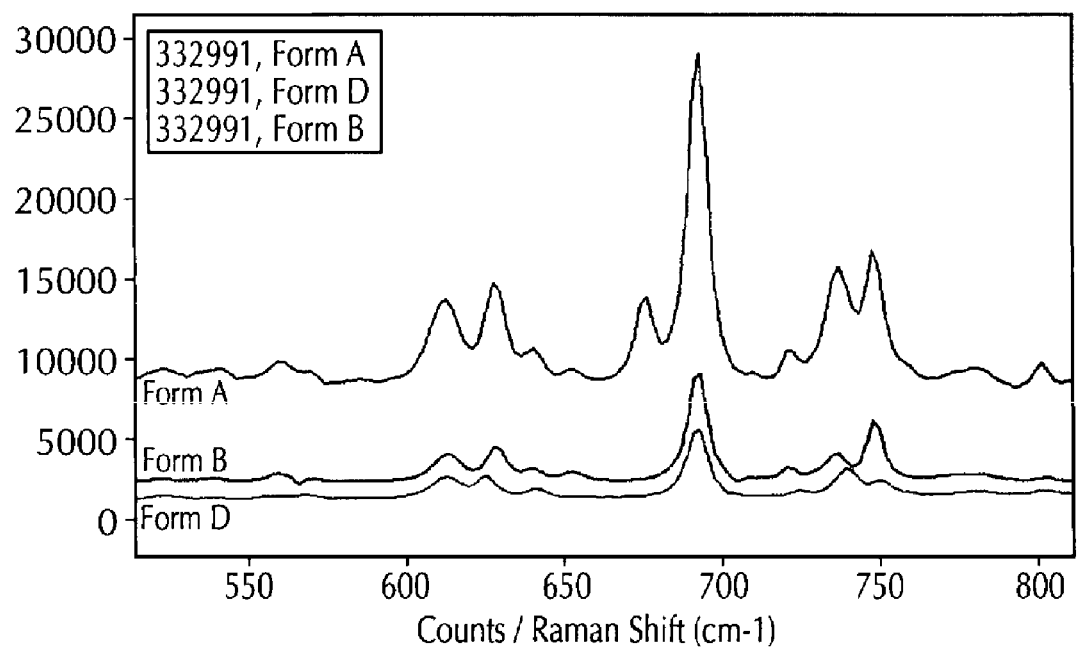
FIG. 10 shows Raman spectra of a mono-isethionate salt (Form A, Form B, and Form D) of 6-acetyl-8-cyclopentyl-5-methyl-2-(5-piperazin-1-yl-pyridin-2-ylamino)-8H-pyrido[2,3-d]pyrimidin-7-one, having Raman Shifts ranging from 500 cm$^{-1}$ to 850 cm$^{-1}$.
Figure 11:
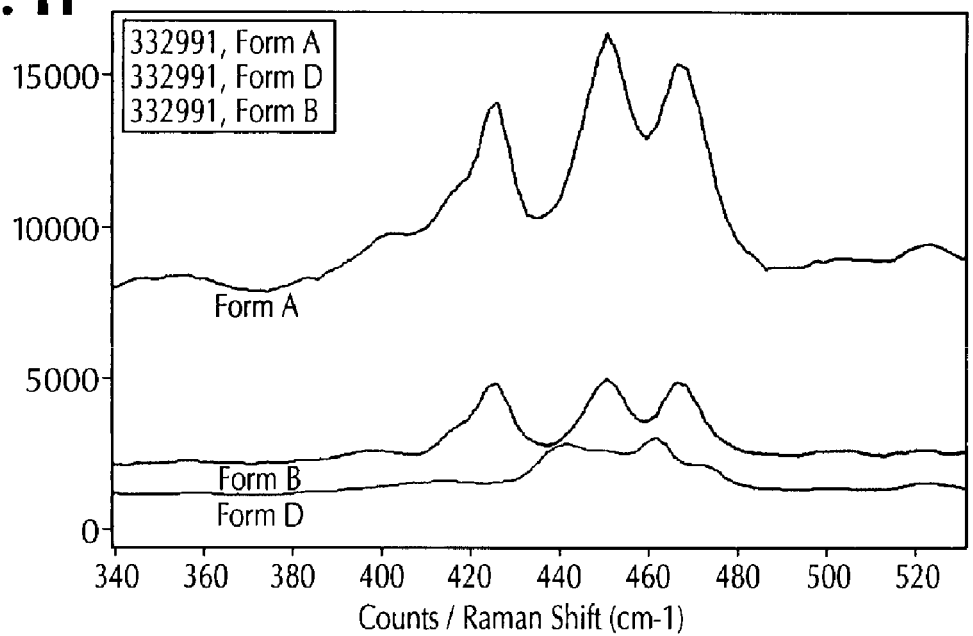
FIG. 11 shows Raman spectra of a mono-isethionate salt (Form A, Form B, and Form D) of 6-acetyl-8-cyclopentyl-5-methyl-2-(5-piperazin-1-yl-pyridin-2-ylamino)-8H-pyrido[2,3-d]pyrimidin-7-one, having Raman Shifts ranging from 340 cm$^{-1}$ to 550 cm$^{-1}$.

FIG. 7-FIG. 11 show Raman spectra of the mono-isethionate salt forms of 6-acetyl-8-cyclopentyl-5-methyl-2-(5-piperazin-1-yl-pyridin-2-ylamino)-8H-pyrido[2,3-d]pyrimidin-7-one (Formula 2). FIG. 7 shows Raman spectra of mono-isethionate salt Form A, Form B, and Form D for Raman Shifts ranging from 0 $cm^{-1}$ to 1850 $cm^{-1}$, while FIG. 8-FIG. 11 provide Raman spectra for mono-isethionate salt Form A, Form B, and Form D for Raman Shifts ranging from 1350 $cm^{-1}$ to 1800 $cm^{-1}$, 1100 $cm^{-1}$ to 1350 $cm^{-1}$, 500 $cm^{-1}$ to 850 $cm^{-1}$, and 340 $cm^{-1}$ to 550 $cm^{-1}$, respectively. In some of the figures, one or more of the Raman spectra may employ different ordinate scaling (e.g., Form A in FIGS. 7, 8, 10, and 11) or different baselines (e.g., Form A and Form B in FIG. 9) or different ordinate scaling and baselines (FIG. 10) to emphasize differences among the mono-isethionate salt forms.

Table 3, below, lists characteristic peaks of the Raman spectra that may be used to distinguish one mono-isethionate salt form from another. As with the PXRD data, the list of characteristic peaks provided in Table 3 is not the only possible list of characteristic peaks, and persons of ordinary skill in the art of polymorph identification may choose other sets of characteristic peaks that will also distinguish one polymorph from another.

The Raman spectra shown in FIG. 7-FIG. 11 were obtained using a KAISER OPTICAL SYSTEMS HOLOLAB Raman microscope and spectrograph. The Raman spectrograph utilized a solid-state diode laser operating at 785 nm, with an output power of approximately 90 mW. The power delivered to the sample through the microscope objective was approximately 27 mW. A thermoelectrically cooled CCD detector was used to detect the Raman signal. Fiber optic cables connecting the Raman microscope and spectrograph were used to guide the laser excitation light and the Raman scattered light to and from the sample, respectively.

To obtain representative Raman spectra, samples of each of the polymorphic forms were probed at multiple locations or spots. For each sample, Raman spectra were obtained at four or five spots, with four replicate spectra at each spot. As is normally the case with solid samples, data for a given polymorphic form exhibited the most variation in peak intensity, and exhibited comparatively little variation in peak position. For each of the forms, Raman shift values (peak positions as a function of wave number) varied by less than 1 $cm^{-1}$, though as would be expected, peak positions among different forms could vary by more than 1 $cm^{-1}$. At least some of the variation in peak intensity or peak position is thought to arise from differences in the way the laser light strikes different crystals in the sample.

TABLE 3

Characteristic Raman Spectra Peaks for Mono-Isethionate Salt Form A, B, and D

| Peak ($cm^{-1}$) | Peak is characteristic of this polymorph |
|---|---|
| 1600 | A and B |
| 1290 | A and B |
| 675 | A |
| 470 | A and B |
| 463 | D |
| 450 | A and B |
| 425 | A and B |

Like the run-to-run variation described above, the Raman spectra of a particular polymorph that are obtained using different instruments appear to exhibit little variation (i.e., 1 $cm^{-1}$ or less) in peak position, and comparatively greater variation in peak intensity. Given that Raman scattering is independent of the excitation wavelength used, peak positions should be about the same between instruments that use different excitation sources. Peak intensities may vary depending on, among other things, the type of detector or optics, the power of the exciting laser, and the sample position.

Figure 12:
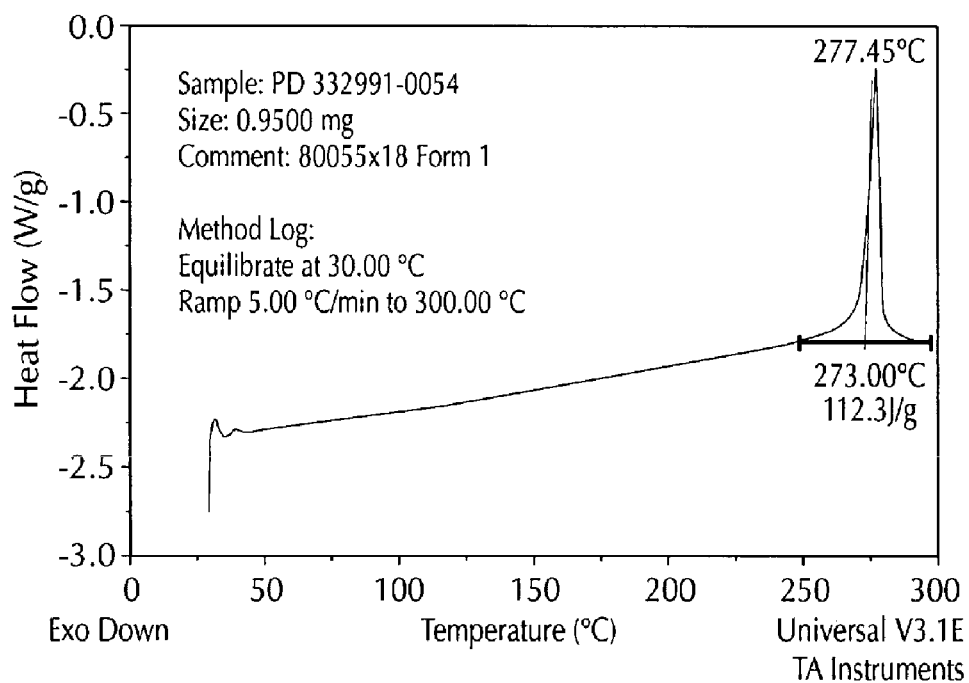
FIG. 12 shows a DSC thermogram of a mono-isethionate salt (Form A) of 6-acetyl-8-cyclopentyl-5-methyl-2-(5-piperazin-1-yl-pyridin-2-ylamino)-8H-pyrido[2,3-d]pyrimidin-7-one.
Figure 13:
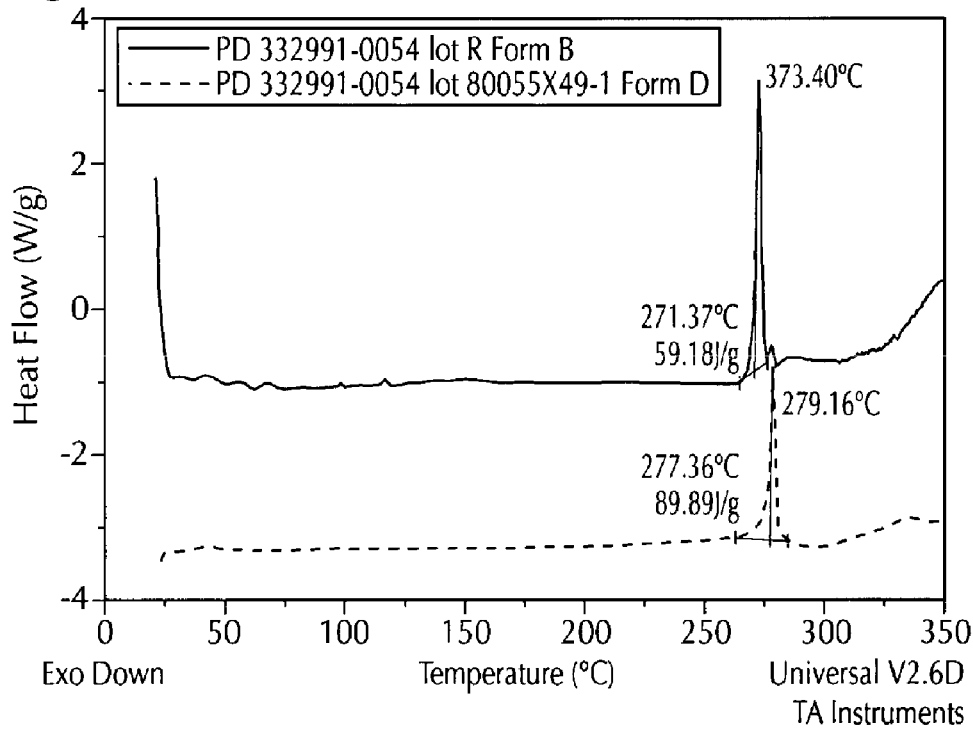
FIG. 13 shows DSC thermograms of a mono-isethionate salt (Form B and Form D) of 6-acetyl-8-cyclopentyl-5-methyl-2-(5-piperazin-1-yl-pyridin-2-ylamino)-8H-pyrido[2,3-d]pyrimidin-7-one.
Figure 14:
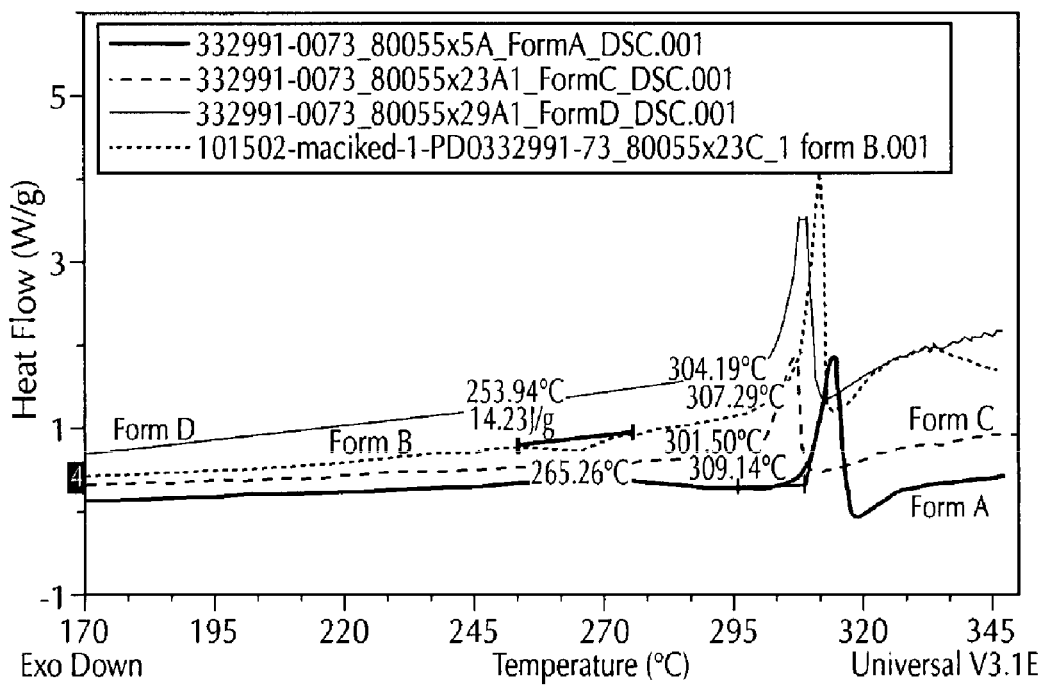
FIG. 14 shows DSC thermograms of a mono-mesylate salt (Form A, Form B, Form C, and Form D) of 6-acetyl-8-cyclopentyl-5-methyl-2-(5-piperazin-1-yl-pyridin-2-ylamino)-8H-pyrido[2,3-d]pyrimidin-7-one.
Figure 15:
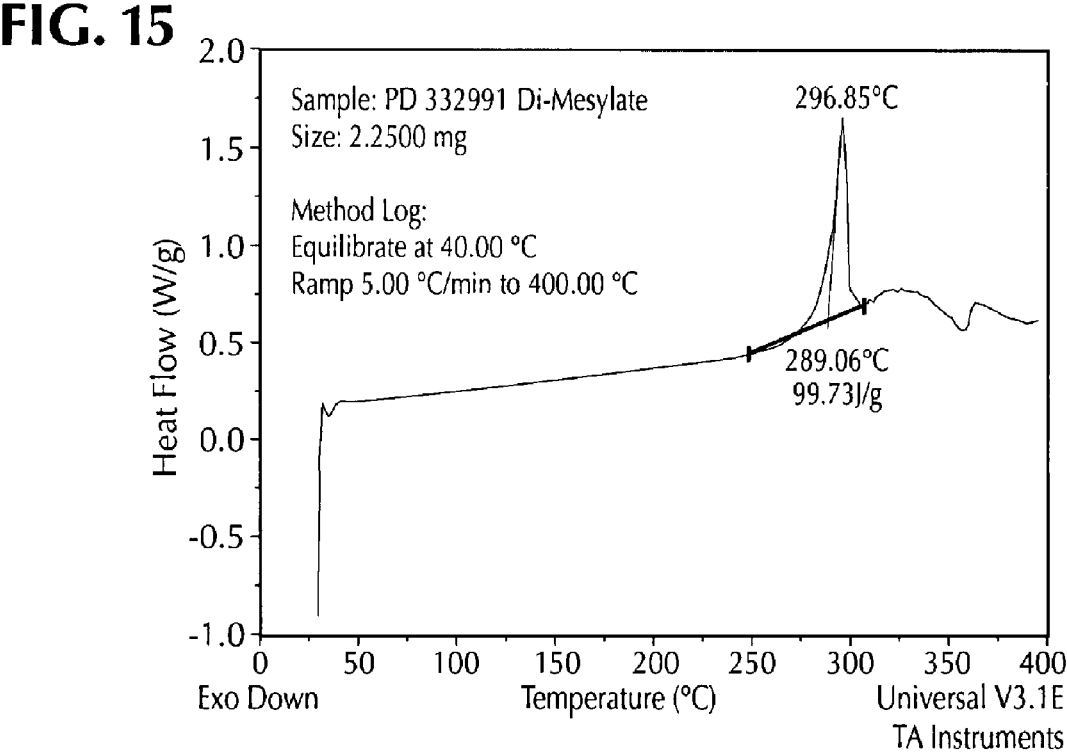
FIG. 15 shows a DSC thermogram of a di-mesylate salt of 6-acetyl-8-cyclopentyl-5-methyl-2-(5-piperazin-1-yl-pyridin-2-ylamino)-8H-pyrido[2,3-d]pyrimidin-7-one.
Figure 16:
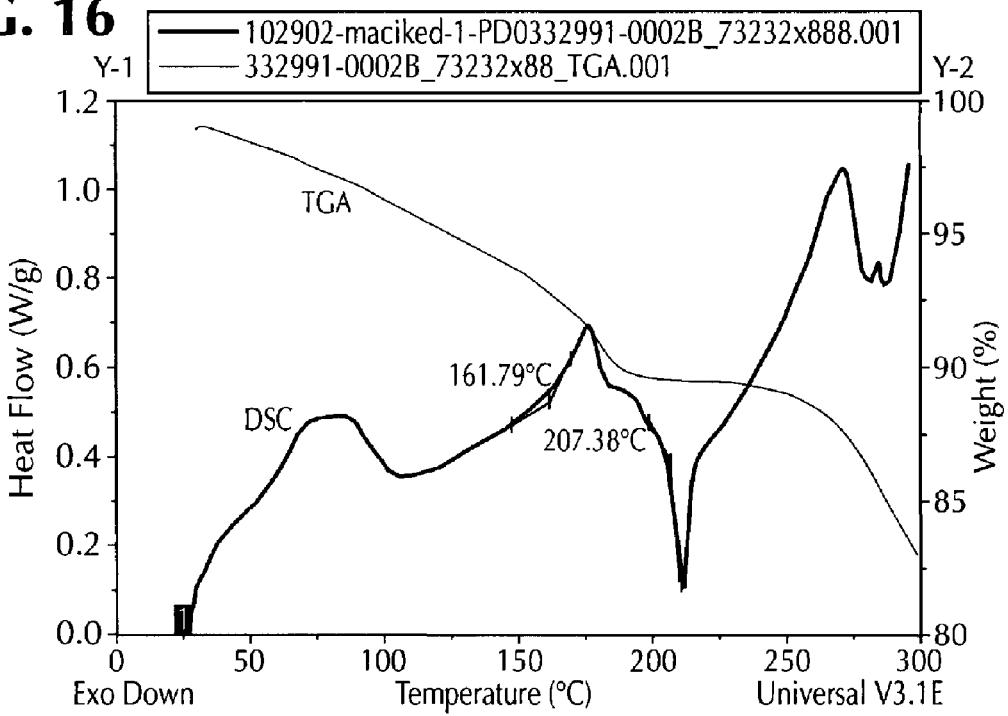
FIG. 16 shows a DSC thermogram of a di-HCl salt of 6-acetyl-8-cyclopentyl-5-methyl-2-(5-piperazin-1-yl-pyridin-2-ylamino)-8H-pyrido[2,3-d]pyrimidin-7-one.

FIG. 12 and FIG. 13 show DSC thermograms of the mono-isethionate salt forms of 6-acetyl-8-cyclopentyl-5-methyl-2-(5-piperazin-1-yl-pyridin-2-ylamino)-8H-pyrido[2,3-d]pyrimidin-7-one (Formula 2) designated as Form A (FIG. 12), and Form B and D (FIG. 13). Additionally, FIG. 14-FIG. 16 show DSC thermograms of the mono-mesylate salt (Form A, B, C, and D), the di-mesylate salt, and the di-HCl salt, respectively. The DSC data were obtained using a TA INSTRUMENTS 2920 Modulated DSC V2.6. Individual polymorph samples were analyzed in vented, sealed aluminum pans using a heating rate of 5° C./min to 350° C. and a nitrogen purge of 50 mL/min.

As shown in FIG. 12-FIG. 15, the mono-isethionate salt (Form A, B, and D), the mono-mesylate salt (Form A, B, C, and D), and the di-mesylate salt have distinct melting points, exhibiting sharp endotherms at about 273° C., 271° C., 277° C., 309° C., 307° C., 302° C., 304° C., and 289° C., respectively. In contrast, the di-HCl salt (FIG. 16) possesses a comparatively complex DSC thermogram, which includes broad endotherms between about 40° C. and 110° C. and between about 160° C. and 200° C., which likely indicate loss of moisture and lattice water, respectively. The di-HCl salt DSC trace also exhibits a relatively sharp exotherm starting at about 207° C. and a broad endotherm beginning at about 275° C., which probably indicate, respectively, form transformation and melting or decomposition or both.

Figure 17:
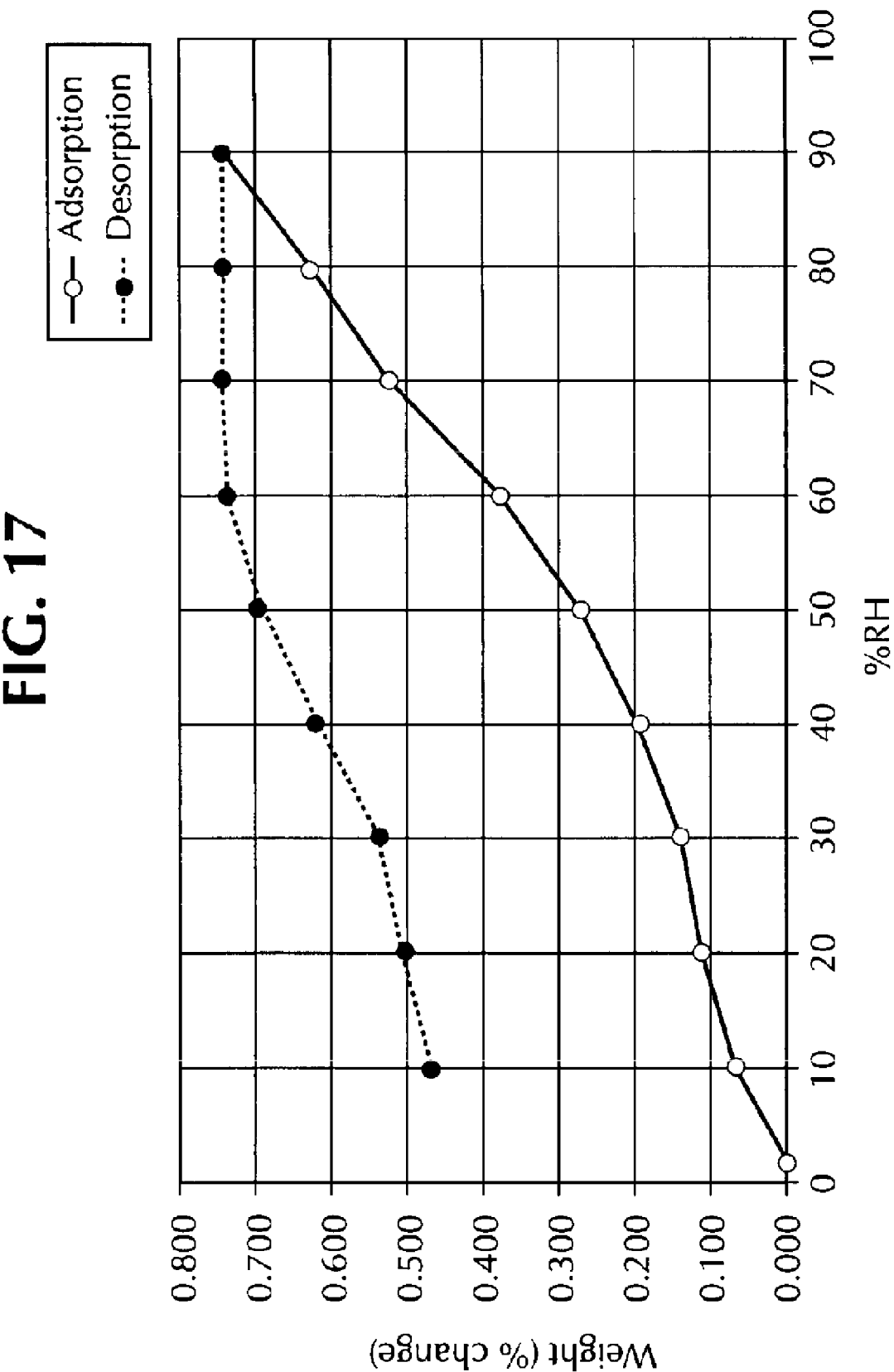
FIG. 17 shows water adsorption/desorption isotherms for the free base of 6-acetyl-8-cyclopentyl-5-methyl-2-(5-piperazin-1-yl-pyridin-2-ylamino)-8H-pyrido[2,3-d]pyrimidin-7-one.
Figure 18:
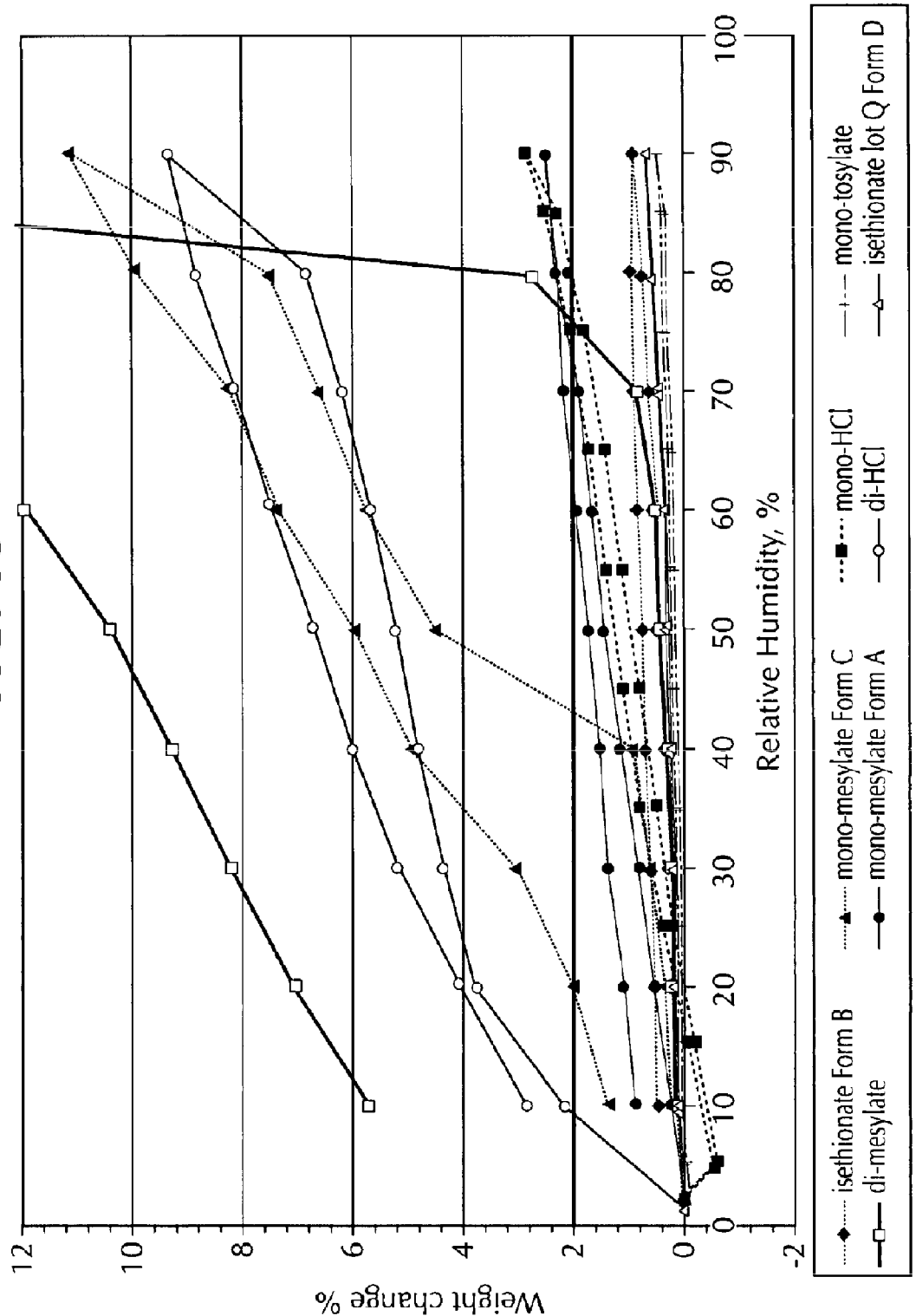
FIG. 18 shows water adsorption/desorption isotherms for various salts of 6-acetyl-8-cyclopentyl-5-methyl-2-(5-piperazin-1-yl-pyridin-2-ylamino)-8H-pyrido[2,3-d]pyrimidin-7-one, including mono-isethionate (Form B and Form D), mono- and di-HCl, mono-mesylate (Form A and Form C), di-mesylate, and mono-tosylate.

FIG. 17 and FIG. 18 show water adsorption and desorption isotherms (at 25° C.) for the free base (Formula 1) and various salts of 6-acetyl-8-cyclopentyl-5-methyl-2-(5-piperazin-1-yl-pyridin-2-ylamino)-8H-pyrido[2,3-d]pyrimidin-7-one, including mono-isethionate (Form B and D), mono- and di-HCl, mono-mesylate (Form A and C), di-mesylate, and mono-tosylate. The water adsorption and desorption data were obtained using a VTI CORPORATION MODEL SGA-100 symmetrical gravimetric analyzer. To obtain a water vapor isotherm, a sample of a polymorph was placed on a microbalance in a sealed environmental chamber, and subsequently heated at a rate of 5° C./min until the temperature in the chamber reached 40° C. To obtain a dry sample weight, the polymorph was allowed to equilibrate at 40° C. until the sample experienced a weight change less than 0.0270 wt % in 2 min. Following drying, the sample was cooled to 25° C. and subsequently exposed to different humidity levels ranging from 5 or 10% RH to 90% RH and from 90% RH to 10 or 5% RH, in 10% RH increments. At each humidity level, the polymorph was allowed to equilibrate until the sample experienced a weight change less than 0.0270 wt % in 2 min. The equilibrium mass at each humidity level was recorded and, along with the dry sample weight, used to generate a plot of weight change versus relative humidity.

Of the compounds shown in FIG. 17 and FIG. 18, only the free base, the mono-isethionate salt (Form B and D), and mono-tosylate salt exhibit less than a 2% change in mass when exposed to humidity levels ranging from 10% RH to 90% RH at 25° C.

Table 4 lists solubility in water of the freebase (its most stable crystal phase according to slurry experiments) and the isethionate salt (Form B, its most stable form according to results of slurry experiments). Since Form B appears to be the most stable isethionate salt form, it should exhibit the lowest water solubility among the isethionate salt forms observed. The other isethionate salt forms were not evaluated for metastable solubility. Aqueous solubility for the isethionate salt was obtained by dissolving the salt in water up to approximately 300 mg/mL, equilibrating for about 48 h after which time some solid was observed, and measuring the aqueous phase salt concentration using HPLC. See Table 5 for a list of HPLC conditions. Aqueous solubility for the freebase was obtained by equilibrating the solid in water for 14 h and measuring the aqueous phase free base concentration using a semi-automated UV-vis method, which utilized a SPECTRMAX PLUS spectrophotometer plate reader.

The data in Table 4 indicates that the water solubility of the mono-isethionate salt (at pH 5.4) is more than 20,000-fold higher than the freebase (at pH 7.9). This large disparity in water solubility cannot be explained by the relatively modest difference in pH of the saturated solutions of the freebase and the mono-isethionate salt. Indeed, the theoretical water solubility of the freebase is only 0.62 mgA/mL at pH 5.4 by Henderson-Hasselbalch calculation (using free base solubility 0.0092 mg/mL at pH 7.9 and $pK_a$s 7.3 and 4.1). Seeding an aqueous solution of the mono-isethionate salt prepared at 117 mgA/mL, pH 5.4 (supersaturated with respect to free base) with crystals of the freebase did not cause precipitation. Instead, the seeds dissolved, indicating some ability of the isethionate ion to solubilize the freebase in water.

TABLE 4

Water Solubility of the Free Base and Isethionate Salt (Form B)

| Sample | Solubility mgA/mL | Final pH | Equilibration Time h |
|---|---|---|---|
| Free base | 0.009 | 7.9 | 14 |
| isethionate | 213 | 5.4 | 48 |

TABLE 5

General HPLC Conditions for Water Solubility Measurements

| Control Variable | Value |
|---|---|
| Column Flow Rate | 1 mL/min |
| Stop Time | 45 min |
| Solvent A | 10 mM Acetate, pH 5.7 |
| Solvent B | ACN |
| Solvent A/Solvent B (v/v) | |
| 0 min | 80/20 |
| 30 min | 25/75 |
| 35 min | 25/75 |
| 36 min | 80/20 |
| 45 min | 80/20 |
| Detection Wavelength | 260 nm |
| Column Injection Volume | 10 μL |
| Column Temperature | 25° C. |
| Column Type (YMC PAC PRO) | C18 150 × 4.6 mm, 3μ particle size |

The solubility of the isethionate salt in normal saline is 0.58 mgA/mL, which is much less than its water solubility, and is very close to the theoretical value 0.43 mgA/mL (Henderson-Hasselbalch calculation) at the final pH of this solution (pH 5.56). In normal saline, the surprising solubilizing power of the isethionate ion essentially disappears and the compound solubility behaves more like a typical basic compound.

The isethionate salt can be prepared using a number of techniques. For example, in one method, a solution of isethionic acid and a first solvent is admixed with an aqueous slurry of 6-acetyl-8-cyclopentyl-5-methyl-2-(5-piperazin-1-yl-pyridin-2-ylamino)-8H-pyrido[2,3-d]pyrimidin-7-one. The mixture is filtered to remove any solids, and the resulting filtrate is freeze-dried (lyophilized) to give an amorphous isethionate salt. The amorphous salt is converted to a crystalline form by dissolving it in a second solvent, which may be accompanied by heating to promote complete dissolution. The resulting solution is subsequently cooled to RT or less to precipitate a crystalline form of the salt, which can be isolated via filtration and then dried in a vacuum oven.

The method generally employs stoichiometric (i.e., molar ratios of 1:1 or 2:1) or near stoichiometric amounts of isethionic acid and 6-acetyl-8-cyclopentyl-5-methyl-2-(5-piperazin-1-yl-pyridin-2-ylamino)-8H-pyrido[2,3-d]pyrimidin-7-one. The first and second solvents may be the same or different, and are typically water-miscible solvents, including alcohols such as MeOH and EtOH. The amount of heating necessary to dissolve the amorphous salt in the second solvent will depend on the solvent used, but the temperature of the mixture is typically in the range of about 30° C. to about 60° C., and is normally in the range of about 30° C. to about 50° C. In some cases, the temperature of the mixture is in the range of about 30° C. to about 40° C. or about 35° C. to about 40° C.

In another method, the free base (Formula 1) is dispersed (slurried) in a first solvent and is seeded with a crystalline isethionate salt form. The resulting mixture is admixed with a solution of isethionic acid and a second solvent. Typically, the isethionic acid solution is added in multiple portions over a period of time. The resulting slurry or dispersion is stirred at RT or above, usually at a temperature greater than about 35° C. or 40° C. To improve yield, the resulting mixture can be cooled to a temperature below about 0° C., which precipitates additional isethionate salt crystals. The isethionate salt crystals that can be isolated via filtration and then dried in a vacuum oven. Like the method described above, this technique employs stoichiometric or near stoichiometric amounts of isethionic acid and 6-acetyl-8-cyclopentyl-5-methyl-2-(5-piperazin-1-yl-pyridin-2-ylamino)-8H-pyrido[2,3-d]pyrimidin-7-one. In addition, the first and second solvents may be the same or different, and are typically water-miscible solvents, including alcohols such as MeOH and EtOH. Compared to the previously described process, this method often results in improved yields and better (e.g., larger, more uniform) crystals.

Another method bypasses the free base (Formula 1) and generates the isethionate salt directly from a protected process intermediate. The method includes reacting an N-BOC protected compound of Formula 3,

3

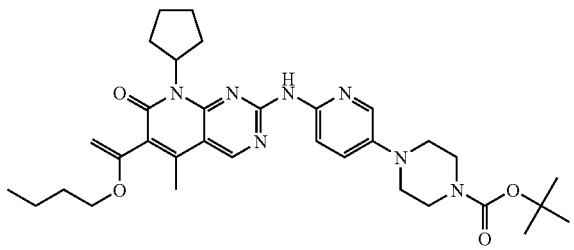

with about 3.5 equivalents (or more) of isethionic acid in a first solvent and water, which removes the BOC protecting group and unmasks an acetyl group to give a di-isethionate salt of 6-acetyl-8-cyclopentyl-5-methyl-2-(5-piperazin-1-yl-pyridin-2-ylamino)-8H-pyrido[2,3-d]pyrimidin-7-one. The reaction can be carried out at room temperature or higher, and is often carried out at a temperature ranging from about 30° C. to about 60° C. To this reaction mixture is added a hindered base (e.g., Et$_3$N) in a second solvent, which forms a salt with the isethionic acid that is soluble in the reaction mixture. The amount of base added is sufficient to maintain—in the presence of the di-isethionate salt—a slight excess of free isethionic acid in the reaction mixture. For example, if 3.5 equivalents of isethionic acid were reacted with the BOC-protected compound of Formula 3, about 1.45 equivalents of the hindered base could be used, resulting in about 0.05 equivalents excess of the free isethionic acid. If desired, the di-isethionate salt can be isolated by filtration.

To obtain a mono-isethionate salt of 6-acetyl-8-cyclopentyl-5-methyl-2-(5-piperazin-1-yl-pyridin-2-ylamino)-8H-pyrido[2,3-d]pyrimidin-7-one, additional base is added over an extended period of time (e.g., dropwise) to ensure formation of the requisite mono-isethionate salt form (e.g., Form B). Adding the hindered base too quickly may cause formation of other, metastable polymorphs. To improve yield, the resulting slurry can be cooled to a temperature of about 5° C. or below, and then filtered and dried. As in the methods described above, the first and second solvents may be the same or different, and are water-miscible solvents, including alcohols such as MeOH and EtOH.

The other disclosed salt forms—e.g., mono- or di-HCl, mesylate, or tosylate salts—can be prepared in a similar manner to the methods described above for the isethionate salt (Formula 2).

The disclosed compounds (Formula 1 and salts) embrace all pharmaceutically acceptable isotopic variations. An isotopic variation is a compound in which at least one atom is replaced by an atom having the same atomic number, but an atomic mass different from the atomic mass usually found in nature. Useful isotopes include isotopes of hydrogen, carbon, nitrogen, oxygen, phosphorus, sulfur, fluorine, and chlorine. Exemplary isotopes thus include, without limitation, $^2$H, $^3$H, $^{13}$C, $^{14}$C, $^{15}$N, $^{17}$O, $^{18}$O, $^{32}$P, $^{35}$S, $^{18}$F, and $^{36}$Cl.

Substitution of the disclosed compounds with isotopes such as deuterium, i.e. $^2$H, may afford certain therapeutic advantages resulting from greater metabolic stability, for example, increased in vivo half-life or reduced dosage requirements, and hence may be more useful in some circumstances. In addition, certain isotopic variations, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Isotopic variations of the disclosed compounds can generally be prepared by conventional techniques known to those skilled in the art or by processes analogous to those described in the accompanying Examples using appropriate isotopic variations of suitable reagents. Pharmaceutically acceptable solvates of the disclosed compounds include those in which the solvent of crystallization may be isotopically substituted, e.g. D$_2$O, d$_6$-acetone, d$_6$-DMSO.

The disclosed compounds (Formula 1 and salts) may be administered as crystalline or amorphous products. They may be obtained, for example, as solid plugs, powders, or films by methods such as precipitation, crystallization, freeze-drying, spray drying, or evaporative drying. Microwave or radio frequency drying may be used for this purpose.

The disclosed compounds may be administered alone or in combination with other drugs and will generally be administered as a formulation in association with one or more pharmaceutically acceptable excipients. The term "excipient" describes any ingredient other than the compounds represented by Formula 1 and its salts. The choice of excipient will to a large extent depend on the particular mode of administration.

The disclosed compounds may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations. Liquid formulations include suspensions, solutions, syrups and elixirs. Such formulations may be employed as fillers in soft or hard capsules and typically comprise a carrier, for example, water, EtOH, polyethylene glycol, propylene glycol, methylcellulose, or a suitable oil, and one or more emulsifying agents and/or suspending agents. Liquid formulations may also be prepared by the reconstitution of a solid, for example, from a sachet.

The disclosed compounds may also be used in fast-dissolving, fast-disintegrating dosage forms such as those described in Liang and Chen, *Expert Opinion in Therapeutic Patents* (2001) 11(6):981-986.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methylcellulose, microcrystalline cellulose, lower alkyl-substituted hydroxypropyl cellulose, starch, pregelatinized starch, and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose, and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch, and dibasic calcium phosphate dihydrate.

Tablets may also optionally include surface-active agents, such as sodium lauryl sulfate and polysorbate 80, and glidants such as silicon dioxide and talc. When present, surface-active agents may comprise from 0.2 wt % to 5 wt % of the tablet, and glidants may comprise from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulfate. Lubricants generally comprise from 0.25 wt % to 10 wt %, preferably from 0.5 wt % to 3 wt % of the tablet. Other ingredients may include preservatives, antioxidants, flavors, and colorants.

Tablet blends may be directly compressed to form tablets. Tablet blends or portions of blends may alternatively be wet-, dry-, or melt-granulated, melt congealed, or extruded before tabletting. The final formulation may comprise one or more layers and may be coated or uncoated. Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant. For additional details concerning the formulation of tablets, see H. Lieberman and L. Lachman, *Pharmaceutical Dosage Forms: Tablets, Vol.* 1 (1980).

Solid formulations for oral administration may be formulated to be immediate and/or modified release. Modified release formulations include delayed-, sustained-, pulsed-, controlled-, targeted-, and programmed-release. For a general description of suitable modified release formulations, see U.S. Pat. No. 6,106,864. For details of other useful release technologies, such as high energy dispersions and osmotic and coated particles, see Verma et al, *Pharmaceutical Technology On-line* (2001) 25(2):1-14. For a discussion of the use of chewing gum to achieve controlled release, see WO 00/35298.

The disclosed compounds (Formula 1 and salts) may also be administered directly into the blood stream, into muscle, or into an internal organ. Suitable means for parenteral administration include intravenous, intra-arterial, intraperitoneal, intrathecal, intraventricular, intraurethral, intrasternal, intracranial, intramuscular, and subcutaneous. Suitable devices for parenteral administration include needle (including micro-needle) injectors, needle-free injectors and infusion techniques.

Parenteral formulations are typically aqueous solutions which may contain excipients such as salts, carbohydrates, and buffering agents (preferably to a pH of from 3 to 9), but for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art.

The solubility of the disclosed compounds used in the preparation of parenteral solutions may be increased by the use of appropriate formulation techniques, such as the incorporation of solubility-enhancing agents. Formulations for parenteral administration may be formulated to be immediate and/or modified release as described above. Thus the disclosed compounds may be formulated in a more solid form for administration as an implanted depot providing long-term release of the active compound.

The compounds of the invention may also be administered topically to the skin or mucosa, either dermally or transdermally. Typical formulations for this purpose include gels, hydrogels, lotions, solutions, creams, ointments, dusting powders, dressings, foams, films, skin patches, wafers, implants, sponges, fibers, bandages, and microemulsions. Liposomes may also be used. Typical carriers include alcohol, water, mineral oil, liquid petrolatum, white petrolatum, glycerin, polyethylene glycol and propylene glycol. Topical formulations may also include penetration enhancers. See, for example, Finnin and Morgan, *J Pharm Sci* (1999) 88(10):955-958.

Other means of topical administration include delivery by iontophoresis, electroporation, phonophoresis, sonophoresis and needle-free (e.g. POWDERJECT) or micro-needle injection. Formulations for topical administration may be formulated to be immediate and/or modified release as described above.

The disclosed compounds can also be administered intranasally or by inhalation, typically in the form of a dry powder (either alone, as a mixture, for example, in a dry blend with lactose, or as a mixed component particle, for example, mixed with phospholipids) from a dry powder inhaler or as an aerosol spray from a pressurized container, pump, spray, atomizer (preferably an atomizer using electrohydrodynamics to produce a fine mist), or nebulizer, with or without the use of a suitable propellant, such as dichlorofluoromethane. The pressurized container, pump, spray, atomizer, or nebulizer contains a solution or suspension, which comprises the active compound, an agent for dispersing, solubilizing, or extending release of the active compound (e.g., EtOH or aqueous EtOH), one or more solvents, which serve as a propellant, and an optional surfactant, such as sorbitan trioleate or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules, blisters and cartridges (made, for example, from gelatin or hydroxypropylmethyl cellulose) for use in an inhaler or insufflator may be formulated to contain a powder mix of the active compound, a suitable powder base such as lactose or starch, and a performance modifier such as L-leucine, mannitol, or magnesium stearate. The lactose may be anhydrous or, preferably, monohydrated. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 µg to 20 mg of the compound of the invention per actuation and the actuation volume may vary from 1 μl to 100 μl. A typical formulation may comprise a compound of Formula 1 or Formula 2, propylene glycol, sterile water, EtOH, and NaCl. Alternative solvents, which may be used instead of propylene glycol, include glycerol and polyethylene glycol.

Formulations for inhaled/intranasal administration may be formulated to be immediate and/or modified release using, for example, poly(DL-lactic-coglycolic acid (PGLA). Suitable flavors, such as menthol and levomenthol, or sweeteners, such as saccharin or saccharin sodium, may be added to formulations intended for inhaled/intranasal administration.

In the case of dry powder inhalers and aerosols, the dosage unit is determined by means of a valve that delivers a metered amount. Units in accordance with the invention are typically arranged to administer a metered dose or "puff" containing from 100 to 1000 μg of the active pharmaceutical ingredient. The overall daily dose will typically be in the range. 100 μg to 10 mg which may be administered in a single dose or, more usually, as divided doses throughout the day.

The active compounds may be administered rectally or vaginally, for example, in the form of a suppository, pessary, or enema. Cocoa butter is a traditional suppository base, but various alternatives may be used as appropriate. Formulations for rectal/vaginal administration may be formulated to be immediate and/or modified release as described above.

The disclosed compounds may also be administered directly to the eye or ear, typically in the form of drops of a micronized suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer (e.g., hydroxypropylmethylcellulose, hydroxyethylcellulose, or methyl cellulose), or a heteropolysaccharide polymer (e.g., gelan gum), may be incorporated together with a preservative, such as benzalkonium chloride. Such formulations may also be delivered by iontophoresis. Formulations for ocular/andial administration may be formulated to be immediate and/or modified release as described above.

The disclosed compounds may be combined with soluble macromolecular entities such as cyclodextrin or polyethylene glycol-containing polymers to improve their solubility, dissolution rate, taste masking, bioavailability and/or stability. Drug-cyclodextrin complexes, for example, are found to be generally useful for most dosage forms and administration routes. Both inclusion and non-inclusion-complexes may be used. As an alternative to direct complexation with the drug, the cyclodextrin may be used as an auxiliary additive, i.e. as a carrier, diluent, or solubilizer. Alpha-, beta- and gamma-cyclodextrins are commonly used for these purposes. See, for example, International Patent Applications WO 91/11172, WO 94/02518, and WO 98/55148.

The therapeutically effective dose of the compounds of Formula 1, Formula 2 or other salts will vary from approximately 0.01 mg/kg to approximately 100 mg/kg of body weight per day. Typical adult doses will be approximately 0.1 mg to approximately 3000 mg per day. The quantity of active component in a unit dose preparation may be varied or adjusted from approximately 0.1 mg to approximately 500 mg, preferably from about 0.6 mg to 100 mg according to the particular application and the potency of the active component. The composition can, if desired, also contain other compatible therapeutic agents. A subject in need of treatment is administered a dosage of about 0.6 to about 500 mg per day, either singly or in multiple doses over a 24-hour period. Such treatment may be repeated at successive intervals for as long as necessary.

EXAMPLES

The following examples are intended to be illustrative and non-limiting, and represent specific embodiments of the present invention.

Example 1

Preparation of 4-[6-(6-bromo-8-cyclopentyl-5-methyl-7-oxo-7,8-dihydro-pyrido[2,3-d]pyrimidin-2-ylamino)-pyridin-3-yl]-piperazine-1-carboxylic acid tert-butyl ester A suspension of 6-bromo-8-cyclopentyl-2-methansulfinyl-5-methyl-8H-pyrido[2,3-d]pyrimidin-7-one (10.00 g, 0.027 mol, prepared as in Example 6 of WO 01/707041, which is incorporated herein by reference) and 10.37 g (0.0373 mol) of 4-(6-amino-pyridin-3-yl)-piperazine-1-carboxylic acid tert-butyl ester in toluene (100 mL) was heated under nitrogen in an oil bath for 7 hours. Thin layer chromatography ($SiO_2$, 10% MeOH/DCM) indicated the presence of both starting materials. The suspension was heated under reflux for an additional 18 hours. The resulting suspension was cooled to RT and filtered to give 4-[6-(6-bromo-8-cyclopentyl-5-methyl-7-oxo-7,8-dihydro-pyrido[2,3-d]pyrimidin-2-ylamino)-pyridin-3-yl]-piperazine-1-carboxylic acid tert-butyl ester (5.93 g, 38%). Melting point>250° C. MS (APCI) $M^++1$: calc'd, 584.2, found, 584.2.

Example 2

Preparation of 4-{6-[8-cyclopentyl-6-(1-ethoxy-vinyl)-5-methyl-7-oxo-7,8-dihydro-pyrido[2.3-d]pyrimidin-2-ylamino]-pyridin-3-yl}-piperazine-1-carboxylic acid tert-butyl ester A suspension of 4-[6-(6-bromo-8-cyclopentyl-5-methyl-7-oxo-7,8-dihydro-pyrido[2,3-d]pyrimidin-2-ylamino)-pyridin-3-yl]-piperazine-1-carboxylic acid tert-butyl ester (5.93 g, 0.010 mol, prepared as in Example 1), tetrakis (triphenylphosphine)palladium(0) (1.40 g, 0.00121 mol), and tributyl(1-ethoxyvinyl)tin (5.32 mL, 0.0157 mol) in toluene (30 mL) was heated under reflux for 3.5 hours. The mixture was cooled and filtered to give a solid. Purification of the solid by silica gel chromatography using a gradient of 5%-66% ethyl acetate/hexane over 15 minutes gave 4-{6-[8-cyclopentyl-6-(1-ethoxy-vinyl)-5-methyl-7-oxo-7,8-dihydro-pyrido[2,3-d]pyrimidin-2-ylamino]-pyridin-3-yl}-piperazine-1-carboxylic acid tert-butyl ester as a yellow foam (4.50 g, 78%). MS (APCI) $M^++1$: calc'd 576.2, found, 576.3.

Example 3

Preparation of 6-acetyl-8-cyclopentyl-5-methyl-2-(5-piperazin-1-yl-pyridin-2-ylamino)-8H-pyrido[2,3-d]pyrimidin-7-one hydrochloride Hydrogen chloride gas was bubbled into an ice-bath cooled solution of 4-{6-[8-cyclopentyl-6-(1-ethoxy-vinyl)-5-methyl-7-oxo-7,8-dihydro-pyrido[2,3-d]pyrimidin-2-ylamino]-pyridin-3-yl}-piperazine-1-carboxylic acid tert-butyl ester (4.50 g, 0.00783 mol, prepared as in Example 2) in DCM (100 mL). The resulting suspension was stoppered and stirred at RT overnight, then diluted with diethyl ether (200 mL). The solid was collected by filtration, washed with diethyl ether, and dried to give the hydrochloride salt of 6-acetyl-8-cyclopentyl-5-methyl-2-(5-piperazin-1-yl-pyridin-2-ylamino)-8H-pyrido[2,3-d]pyrimidin-7-one as a yellow solid (4.01 g, 92%). Melting point 200° C. HPLC, C18 reverse phase, 10%-95% gradient of 0.1% TFA/CH$_3$CN in 0.1% TFA/H$_2$O during 22 minutes: 99.0% at 11.04 minutes. MS (APCI) M$^+$+1: calc'd, 448.2, found, 448.3. Anal. calc'd for C$_{24}$H$_{29}$N$_7$O$_2$.2.4H$_2$O.1.85 HCl: C, 51.64; H, 6.44; N, 17.56, Cl (total), 11.75. Found: C, 51.31; H, 6.41; N, 17.20; Cl (total), 12.11.

Example 4

Preparation of a mono-isethionate salt of 6-acetyl-8-cyclopentyl-5-methyl-2-(5-piperazin-1-yl-pyridin-2-ylamino)-8H-pyrido[2.3-d]pyrimidin-7-one (Form B)

To a slurry of 6-acetyl-8-cyclopentyl-5-methyl-2-(5-piperazin-1-yl-pyridin-2-ylamino)-8H-pyrido[2,3-d]pyrimidin-7-one (7.0 g, 15.64 mmol, prepared as in Example 3 following contact with NaOH) dispersed in 250 mL of water was added drop-wise 30 mL of a 0.52 M solution of isethionic acid in MeOH (15.64 mmol) to a pH of 5.2. The solution was filtered through a glass filter (fine) and the clear solution was freeze-dried to give 9.4 g of the amorphous salt. The amorphous salt (3.16 g) was mixed with 25 mL of MeOH and after almost complete dissolution a new precipitate formed. Another 25 mL of MeOH was added and the mixture was stirred at 46° C. to 49° C. for four hours. The mixture was slowly cooled to 32° C. and put in a cold room (+4° C.) overnight. A sample was taken for PXRD, which indicated formation of Form B. The mixture was filtered and the precipitate was dried overnight at 50° C. in a vacuum oven. This furnished 2.92 g of the mono-isethionate salt of the compound of Formula 1 in 92% yield. HPLC-99.25%, PXRD-Form B, CHNS, H-NMR were consistent with the structure.

Example 5

Preparation of a mono-isethionate salt of 6-acetyl-8-cyclopentyl-5-methyl-2-(5-piperazin-1-yl-pyridin-2-ylamino)-8H-pyrido[2.3-d]pyrimidin-7-one (Form B)

MeOH (100 mL) was placed in a 250 mL flask equipped with a mechanical stirrer, thermocouple/controller, condenser, and heating mantle and preheated to 35° C. An amorphous isethionate salt (2 g, prepared as in Example 4) was slowly added in three even portions with a 25 min to 30 min interval between the additions. The reaction mixture was stirred overnight at 35° C. and subsequently cooled. A sample was filtered and examined by PXRD. It was pure Form B. The whole reaction mixture was then used as Form B seeds in a larger scale experiment.

Example 6

Preparation of a mono-isethionate salt of 6-acetyl-8-cyclopentyl-5-methyl-2-(5-piperazin-1-yl-pyridin-2-ylamino)-8H-pyrido[2,3-d]pyrimidin-7-one (Form B)

MeOH (50 mL) was placed in a 250 mL flask equipped with a magnetic stirrer, condenser, thermocouple/controller, and heating mantle, and preheated to 40° C. An amorphous isethionate salt (1 g, prepared as in Example 4) was slowly added in three even portions with 30 min interval between the portions and then stirred overnight at 40° C. The reaction was monitored by in-situ Raman spectroscopy. The sample was taken, filtered and analyzed by PXRD. It was pure Form B by PXRD and Raman spectroscopy. The mixture was cooled to 25° C. at a rate of 3° C./h, cooled to −10° C., filtered, and vacuum dried to furnish 0.85 g of the Form B crystalline product.

Example 7

Preparation of a mono-isethionate salt of 6-acetyl-8-cyclopentyl-5-methyl-2-(5-piperazin-1-yl-pyridin-2-ylamino)-8H-pyrido[2,3-d]pyrimidin-7-one (Form B)

The free base (Formula 1, 0.895 mg, 2 mmol) was mixed with 10 mL of MeOH and seeded with 33 mg of a mono-isethionate salt of the compound of Formula 1 (Form B). Then 5.6 mL of a 0.375 M solution of isethionic acid in MeOH (2.1 mmol) was added in 10 even portions over 75 min time period. The mixture was stirred for an additional hour and a sample was taken for PXRD analysis. It confirmed formation of crystalline Form B. The mixture was stirred at RT overnight and another PXRD was taken. There was no change in the crystal form. The mixture was cooled in a refrigerator at −8° C. overnight, filtered, and dried at 50° C. in a vacuum oven to give 1.053 g (91.8% of theory) of the above-named compound (Form B). HPLC—99.8%, CHNS, H-NMR, IR are consistent with the structure, PXRD-Form B.

Example 8

Preparation of a mono-isethionate salt of 6-acetyl-8-cyclopentyl-5-methyl-2-(5-piperazin-1-yl-pyridin-2-ylamino)-8H-pyrido[2.3-d]pyrimidin-7-one (Form A)

An amorphous isethionate salt (47 mg, prepared as in Example 4) was mixed with 4 mL of EtOH in a 15 mL flask equipped with a magnetic stirrer, thermocouple and condenser. The mixture was heated to reflux, which resulted in the formation of a nearly clear solution. After refluxing for 10-15 min, the mixture became cloudy. It was slowly cooled to 50° C. and was seeded at 69° C. with Form A. The mixture was held at 50° C. for 5 h and was allowed to cool to RT overnight. The mixture was subsequently cooled to 1° C. with an ice bath, held for 1.5 h, filtered, washed with 0.5 mL of cold EtOH, air-dried, and then dried in a vacuum oven at 70° C. overnight to furnished 38.2 mg of a fine crystalline material. The crystalline material was found to be mono-isethionate salt Form A by PXRD. H-NMR was consistent for the mono-isethionate salt and indicated the presence of residual EtOH ca. 5.9 mol % or 0.6 wt %.

Example 9

Preparation of a mono-isethionate salt of 6-acetyl-8-cyclopentyl-5-methyl-2-(5-piperazin-1-yl-pyridin-2-ylamino)-8H-pyrido[2,3-d]pyrimidin-7-one (Form D)

An amorphous isethionate salt (9.0 g, prepared as in Example 4) was mixed with 300 mL of MeOH, stirred and heated to 63.8° C. (at reflux). To the slightly cloudy mixture was added two 50-mL portions of MeOH. The hot mixture was filtered into a 2-L flask equipped with a mechanical stirrer. The mixture was briefly heated to reflux and then cooled to 60° C. IPA (100 mL) was added to the mixture. The mixture was again heated to 60° C. and an additional 110 mL of IPA was added. A precipitate started to form at 59.7° C. The mixture was reheated to 67.5° C., cooled to 50° C., and held overnight. A sample was taken the next morning for PXRD analysis. The mixture was cooled to 25° C. at a rate of 3° C./h and another PXRD sample was taken when the mixture reached 28° C. The mixture was allowed to cool to RT overnight. A precipitate was collected and dried in a vacuum oven at 65° C. and 30 Torr. The procedure produced 7.45 g (82.8% yield) of the crystalline compound (Form D by PXRD analysis). Previously analyzed samples were also Form D. HPLC showed 98.82% purity and CHNS microanalysis was within +/-0.4%. A slurry of isethionate salt Form A, B, and D in MeOH yielded substantially pure Form B in less than three days.

Example 10

Preparation of isethionic acid (2-hydroxy-ethanesulfonic acid)

A 5-L, four-necked, round-bottomed flask, equipped with mechanical stirrer, thermocouple, gas sparger, and an atmosphere vent through a water trap was charged with 748 g (5.05 mol) of sodium isethionate (ALDRICH), and 4 L of IPA. The slurry was stirred at RT. An ice bath was used to keep the internal temperature below 50° C. as 925 g (25.4 mol) of hydrogen chloride gas (ALDRICH) was sparged into the system at a rate such that it dissolved as fast as it was added (as noted by lack of bubbling through the water trap). Sufficient HCl gas was added until the system was saturated (as noted by the start of bubbling through the water trap). During the addition of HCl, the temperature rose to 45° C. The slurry was cooled to RT and filtered over a coarse-fritted filter. The cake was washed with 100 mL of IPA and the cloudy filtrate was filtered through a 10-20µ filter. The resulting clear, colorless filtrate was concentrated under reduced pressure on a rotary evaporator, while keeping the bath temperature below 50° C. The resulting 1.07 kg of clear, light yellow oil was diluted with 50 mL of tap water and 400 mL of toluene and concentrated under reduced pressure on a rotary evaporator for three days, while keeping the bath temperature below 50° C. The resulting 800 g of clear, light yellow oil was diluted with 500 mL of toluene and 250 mL of IPA and concentrated under reduced pressure on a rotary evaporator for 11 days, keeping the bath temperature below 50° C. The resulting 713 g of clear, light yellow oil was titrated at 81 wt % (580 g, 91.1% yield) containing 7.9 wt % water and 7.5 wt % IPA.

Example 11

Preparation of 4-{6-[6-(1-butoxy-vinyl)-8-cyclopentyl-5-methyl-7-oxo-7,8-dihydro-pyrido[2,3-d]pyrimidin-2-ylamino]-pyridin-3-yl}-piperazine-1-carboxylic acid tert-butyl ester A 5-L, three-necked, round-bottomed flask, equipped with a mechanical stirrer, a thermocouple, and a nitrogen inlet/outlet vented through a silicone oil bubbler was placed under a nitrogen atmosphere and charged with 4-[6-(6-bromo-8-cyclopentyl-5-methyl-7-oxo-7,8-dihydro-pyrido[2,3-d]pyrimidin-2-ylamino)-pyridin-3-yl]-piperazine-1-carboxylic acid tert-butyl ester (300 g, 0.51 mol, prepared as in Example 2), butyl vinyl ether (154 g, 1.54 mol, ALDRICH), n-butanol (1.5 L, ALDRICH), and diisopropyl ethylamine (107 mL, 0.62 mol, ALDRICH). The slurry was placed under approximately 50 Torr vacuum and then refilled with nitrogen 3 times. To this was added 8.3 g (0.01 mol) bis-(diphenylphosphinoferrocene) palladium dichloride dichloromethane (JOHNSON MATTHEY, Lot 077598001) and the resulting slurry was purged an additional three times as described above. The mixture was then heated to 95° C. and stirred for 20 h. The resulting thin red slurry was diluted with 2 L of heptane and cooled to approximately 5° C. At this temperature, 400 mL saturated aqueous potassium carbonate was added and the mixture was filtered and rinsed with 250 mL of heptane. After drying in an oven for 16 h at 45° C., 231.7 g (75% yield) of the title compound was obtained as a yellow solid.

Example 12

Preparation of a mono-isethionate salt of 6-acetyl-8-cyclopentyl-5-methyl-2-(5-piperazin-1-yl-pyridin-2-ylamino)-8H-Pyrido[2,3-d]pyrimidin-7-one (Form B)

A 22-L, three-necked, round-bottomed flask, equipped with a mechanical stirrer, a thermocouple, and a nitrogen inlet/outlet vented through a silicone oil bubbler was placed under a nitrogen atmosphere and charged with 4-{6-[6-(1-butoxy-vinyl)-8-cyclopentyl-5-methyl-7-oxo-7,8-dihydro-pyrido[2,3-d]pyrimidin-2-ylamino]-pyridin-3-yl}-piperazine-1-carboxylic acid tert-butyl ester (725 g, 1.20 mol, prepared as in Example 11) and MeOH (14 L). The slurry was stirred at RT as it was charged with a solution of isethionic acid (530 g, 4.20 mol, prepared as in Example 10), MeOH (1.5 L), and water (70 mL, 3.89 mol). The resulting slurry was heated to 55° C. over 30 minutes and then stirred at 55° C. for 30 minutes. A solution of 175 g (1.73 mol) of $Et_3N$ (ALDRICH) in 200 mL of MeOH was charged to the slurry as it was cooled to 30° C. The slurry was held at 30° C. as a solution of 128 g (1.26 mol) of $Et_3N$ in 2 L of MeOH was added dropwise over 6 hours. The resulting slurry was sampled to determine crystal form (Form B). The slurry was cooled and held at 5° C. for 15 minutes and was subsequently filtered through a coarse-fritted filter. The resulting filter cake was washed with multiple washes of 200 mL of cold MeOH. The solid product was dried at 55° C. under vacuum to yield 710 g (91% yield) of the title compound as yellow crystals.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patents, patent applications, and patent publications, are incorporated herein by reference in their entirety and for all purposes.

The invention claimed is:

1. A method of making a crystalline isethionate salt of 6-acetyl-8-cyclopentyl-5-methyl-2-(5-piperazin-1-yl-pyridin-2-ylamino)-8H-pyrido[2,3-d]pyrimidin-7-one, the method comprising:

combining a solution of isethionic acid and a first solvent with a dispersion of 6-acetyl-8-cyclopentyl-5-methyl-2-(5-piperazin-1-yl-pyridin-2-ylamino)-8H-pyrido[2,3-d]pyrimidin-7-one and water to produce a first mixture;

freeze-drying the first mixture to give an amorphous salt;

mixing the amorphous salt with a second solvent to produce a second mixture that includes a crystalline isethionate salt of 6-acetyl-8-cyclopentyl-5-methyl-2-(5-piperazin-1-yl-pyridin-2-ylamino)-8H-pyrido[2,3-d]pyrimidin-7-one, the second solvent being the same as or different than the first solvent; and optionally heating the second mixture, cooling the second mixture, or heating and cooling the second mixture.

2. A method of making an isethionate salt of 6-acetyl-8-cyclopentyl-5-methyl-2-(5-piperazin-1-yl-pyridin-2-ylamino)-8H-pyrido[2,3-d]pyrimidin-7-one comprising:

providing a seed crystal of an isethionate salt form of 6-acetyl-8-cyclopentyl-5-methyl-2-(5-piperazin-1-yl-pyridin-2-ylamino)-8H-pyrido[2,3-d]pyrimidin-7-one;

adding the seed crystal to a dispersion of 6-acetyl-8-cyclopentyl-5-methyl-2-(5-piperazin-1-yl -pyridin-2-ylamino)-8H-pyrido[2,3-d]pyrimidin-7-one and a first solvent to produce a first mixture;

combining the first mixture with a solution of isethionic acid and a second solvent to produce a second mixture that includes the isethionate salt of 6-acetyl-8-cyclopentyl-5-methyl-2-(5-piperazin-1-yl-pyridin-2-ylamino)-8H-pyrido[2,3-d]pyrimidin-7-one; and optionally heating the second mixture, cooling the second mixture, or heating and cooling the second mixture.

3. The method of claims 1 or 2, wherein the first and second solvents are water miscible.

4. The method of claims 1 or 2, wherein the first and second solvents are alcohols.

5. The method of claims 1 or 2, wherein the first and second solvents are MeOH.

6. The method of claims 1 or 2, wherein the first mixture or the second mixture, respectively, is produced by combining approximately equimolar amounts of isethionic acid and 6-acetyl-8-cyclopentyl-5-methyl-2-(5-piperazin-1-yl-pyridin-2-ylamino)-8H-pyrido[2,3-d]pyrimidin-7-one.

7. The method of claim 1 or 2, further comprising agitating the second mixture at a temperature ranging from about 30° C. to about 60° C.

8. The method of claim 1 or 2, further comprising cooling the second mixture to a temperature at or below about 0° C.

9. A method of making an isethionate salt of 6-acetyl-8-cyclopentyl-5-methyl-2-(5-piperazin-1-yl-pyridin-2-ylamino)-8H-pyrido[2,3-d]pyrimidin-7-one the method comprising: reacting 4-{6-[6-(1-butoxy-vinyl)-8-cyclopentyl-5-methyl-7-oxo-7,8-dihydro-pyrido[2,3-d]pyrimidin-2-ylamino]-pyridin-3-yl}-piperazine-1-carboxylic acid tert-butyl ester with isethionic acid in a first solvent and water to give a mixture that includes a di-isethionate salt of 6-acetyl-8-cyclopentyl-5-methyl-2-(5-piperazin-1-yl-pyridin-2-ylamino)-8H-pyrido[2,3-d]pyrimidin-7-one.

10. The method of claim 9, further comprising adding a hindered base to the reaction mixture to give a mono-isethionate salt of 6-acetyl-8-cyclopentyl-5-methyl-2-(5-piperazin-1-yl-pyridin-2-ylamino)-8H-pyrido[2,3-d]pyrimidin-7-one.

* * * * *